(12) United States Patent
Mihan et al.

(10) Patent No.: US 7,534,847 B2
(45) Date of Patent: May 19, 2009

(54) COPOLYMERS OF ETHYLENE WITH α-OLEFINS

(75) Inventors: Shahram Mihan, Bad Soden (DE); Dieter Lilge, Limburgerhof (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/538,540

(22) PCT Filed: Dec. 18, 2003

(86) PCT No.: PCT/EP03/14437

§ 371 (c)(1),
(2), (4) Date: Jun. 11, 2005

(87) PCT Pub. No.: WO2004/056878

PCT Pub. Date: Jul. 8, 2004

(65) Prior Publication Data

US 2005/0282979 A1      Dec. 22, 2005

Related U.S. Application Data

(60) Provisional application No. 60/451,836, filed on Mar. 4, 2003.

(30) Foreign Application Priority Data

Dec. 20, 2002   (DE)   ................... 102 61 252

(51) Int. Cl.
*C08F 210/16* (2006.01)
*C08L 23/08* (2006.01)

(52) U.S. Cl. .................... 526/348; 525/240; 528/396; 428/364

(58) Field of Classification Search ............... 528/396; 526/348, 352, 169, 192, 161, 129, 172; 502/103, 502/104; 556/53; 525/240
See application file for complete search history.

(56) References Cited

U.S. PATENT DOCUMENTS

| | | | |
|---|---|---|---|
| 3,125,547 A | 3/1964 | Blatz | ............... 260/45.5 |
| 3,242,150 A | 3/1966 | Scoggin | ............... 260/88.2 |
| 3,248,179 A | 4/1966 | Norwood | ............... 23/285 |
| 5,246,783 A * | 9/1993 | Spenadel et al. | ............... 428/461 |
| 5,281,679 A * | 1/1994 | Jejelowo et al. | ............... 526/114 |
| 5,382,630 A * | 1/1995 | Stehling et al. | ............... 525/240 |
| 5,498,581 A * | 3/1996 | Welch et al. | ............... 502/102 |
| 6,240,507 B1 * | 5/2001 | Derrick et al. | ............... 712/217 |
| 6,255,418 B1 | 7/2001 | Jolly et al. | ............... 526/160 |
| 6,350,814 B1 | 2/2002 | Bauer et al. | ............... 525/191 |
| 6,417,302 B1 | 7/2002 | Bohnen | ............... 526/160 |
| 6,420,507 B1 | 7/2002 | Kale et al. | |
| 6,437,161 B1 | 8/2002 | Mihan et al. | ............... 556/11 |
| 6,589,905 B1 | 7/2003 | Fischer et al. | ............... 502/300 |
| 6,642,313 B1 * | 11/2003 | Kazakov et al. | ............... 525/191 |
| 6,723,675 B1 | 4/2004 | Wang | |
| 6,737,130 B2 * | 5/2004 | Ferri | ............... 428/35.2 |
| 6,787,498 B2 | 9/2004 | Mihan et al. | ............... 502/120 |
| 6,812,185 B2 | 11/2004 | Fischer et al. | ............... 502/120 |
| 6,838,563 B2 | 1/2005 | Mihan et al. | ............... 546/10 |
| 6,911,516 B1 | 6/2005 | Mihan et al. | ............... 526/348 |
| 6,919,412 B1 | 7/2005 | Mihan et al. | ............... 526/127 |
| 6,924,248 B2 | 8/2005 | Mihan et al. | ............... 502/132 |
| 2003/0036658 A1 | 2/2003 | Mihan et al. | ............... 548/402 |
| 2003/0036662 A1 | 2/2003 | Mihan et al. | ............... 556/20 |
| 2003/0055267 A1 | 3/2003 | Mihan et al. | ............... 548/402 |
| 2003/0176275 A1 | 9/2003 | Fraaije et al. | ............... 502/103 |
| 2003/0236164 A1 | 12/2003 | Fischer et al. | ............... 502/439 |
| 2004/0033890 A1 | 2/2004 | Mihan et al. | ............... 502/113 |

FOREIGN PATENT DOCUMENTS

| | | |
|---|---|---|
| DE | 19710615 | 9/1998 |
| DE | 19745047 | 4/1999 |
| EP | 0100843 | 2/1984 |
| EP | 0416815 | 3/1991 |
| EP | 0420436 | 4/1991 |
| EP | 608369 | 8/1994 |
| EP | 0662989 | 7/1995 |
| EP | 0728160 | 8/1996 |
| EP | 0742046 | 11/1996 |

(Continued)

OTHER PUBLICATIONS

S. Pang et al., "Size-Exclusion Chromatographic Assessment of Long-Chain Branch Frequency in Polyethylenes," *American Chemical Society*, Chapter 17, p. 254-269 (1993), ACS Symposium Series 521, *Chromatography of Polymers* edited by T. Provder.

(Continued)

*Primary Examiner*—Vasu Jagannathan
*Assistant Examiner*—Rip A. Lee
(74) *Attorney, Agent, or Firm*—Jarrod N Raphael

(57) ABSTRACT

Copolymers of ethylene with α-olefins which have a molar mass distribution $M_w/M_n$ of from 1 to 8, a density of from 0.85 to 0.94 g/cm$^3$, a molar mass $M_n$ of from 10.000 g/mol to 4 000 000 g/mol and a CDBI of less than 50% and in which the side chain branching of the maxima of the individual peaks of the short chain branching distribution is in each case greater than 5 CH$_3$/1 000 carbon atoms, a process for preparing them, a catalyst suitable for preparing them and fibers, moldings, films or polymer mixtures in which these copolymers are present.

6 Claims, 2 Drawing Sheets

FOREIGN PATENT DOCUMENTS

Figure 1:
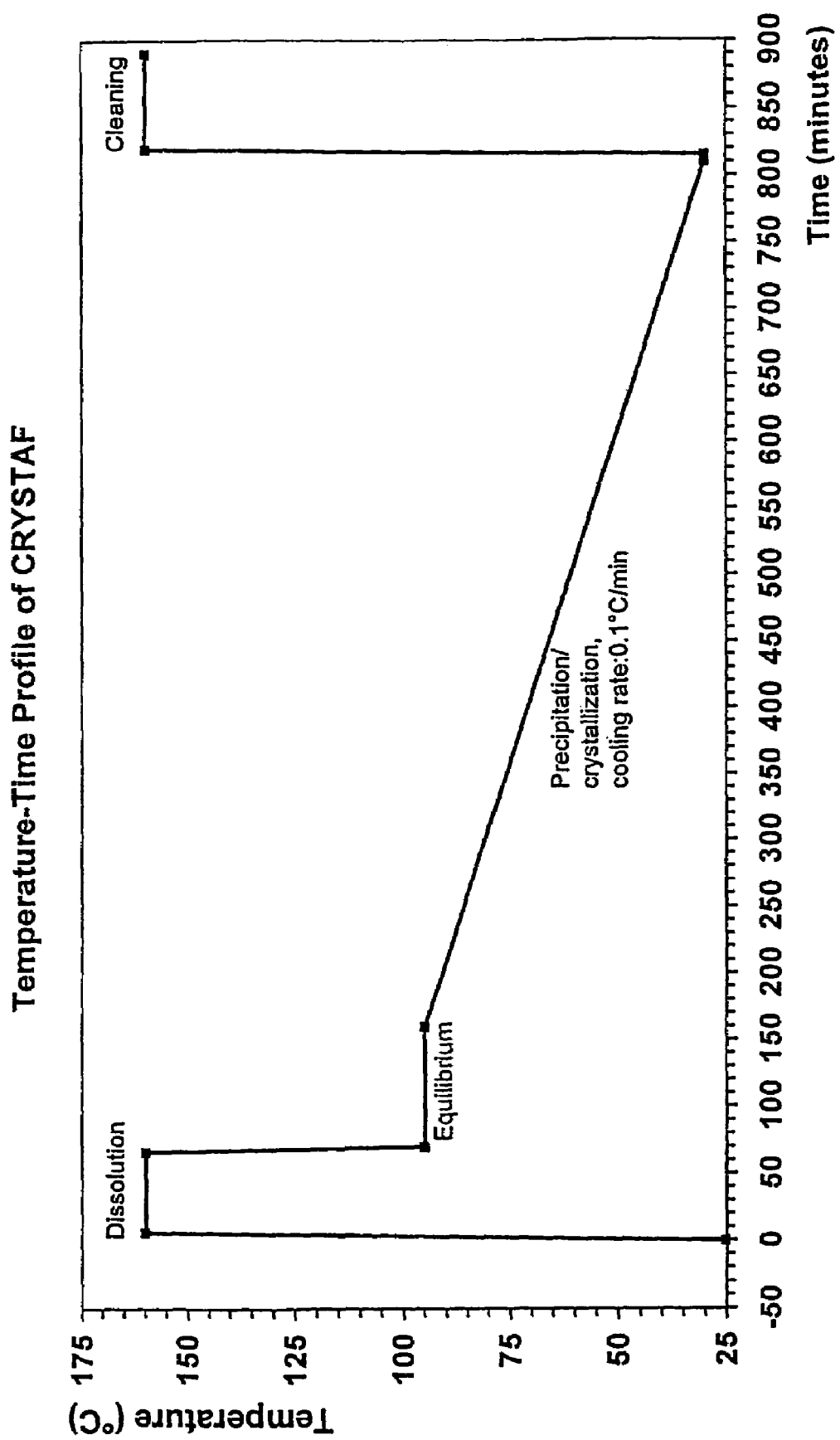

| | | |
|---|---|---|
| EP | 899278 | 3/1999 |
| WO | 9003414 | 4/1990 |
| WO | 9303098 | 2/1993 |
| WO | 9312151 | 6/1993 |
| WO | 9527005 | 10/1995 |
| WO | 9600243 | 1/1996 |
| WO | 9704015 | 2/1997 |
| WO | 9736937 | 10/1997 |
| WO | 9803559 | 1/1998 |
| WO | 9822486 | 5/1998 |
| WO | 9827124 | 6/1998 |
| WO | 9840419 | 9/1998 |
| WO | 9844011 | 10/1998 |
| WO | 9906414 | 2/1999 |
| WO | 0005277 | 2/2000 |
| WO | 0024787 | 5/2000 |
| WO | 0031090 | 6/2000 |
| WO | 0112641 | 2/2001 |
| WO | 0112687 | 2/2001 |
| WO | WO 01/12641 A1 * | 2/2001 |
| WO | 0141920 | 6/2001 |
| WO | 0192346 | 12/2001 |
| WO | 0196417 | 12/2001 |
| WO | WO 01/92346 A2 * | 12/2001 |
| WO | 01/12687 | 2/2002 |

OTHER PUBLICATIONS

L. Wild, "Temperature Rising Elution Fractionation," *Advances in Polymer Science 98*, p. 1-47 (1990).
W. von Freiesleben, "Über eine neue Fulven-Synthese [1]," *Angew Chem.*, vol. 75(12), p. 576 (1963).
R. Halterman, "Synthesis and Applications of Chiral Cyclopentadienylmetal Complexes," *Chem. Rev.*, vol. 92, p. 965-994 (1992).
S. Strauss, "The Search for Larger and More Weakly Coordinating Anions," *Chem. Rev.*, vol. 93(3), p. 927-942 (1993).
M. Enders et al., "8-Quinolylcylopentadienyl, a Ligand with a Tailored Fit for Chelate Complexes," *Chem. Ber.*, vol. 129, p. 459-463 (1996).
B. Monrabal, "Crystallization Analysis Fractionation: A New Technique for the Analysis of Branching Distribution in Polyolefins," *Journal of Applied Polymer Science*, vol. 52, p. 491-499 (1994).
J. Ewen et al., "Expanding the Scope of Metallocene Catalysis: Beyond Indenyl and Fluorenyl Derivatives," p. 150-169 (1999).
M. Enders et al., "New Chromium (III) Complexes as Highly Active Catalysts for Olefin Polymerization," *Organometallics*, vol. 20(24), p. 5005-5007 (2001).
S. Bradley et al., "Synthesis and Structure of Amino-Functionalized Cyclopentadienyl Vanadium Complexes and Evaluation of Their Butadiene Polymerization Behavior," *Organometallics*, vol. 21(16), p. 3443-3453 (2002).
N. Furukawa et al., "Preparation of Pyridyl Grignard Reagents and Cross Coupling Reactions with Sulfoxides Bearing Azaheterocycles," *Tetrahedron Letters*, vol. 28(47), p. 5845-5848 (1987).
L. Brandsma, *Preparative Polar Organometallic Chemistry*, vol. 2, Springer-Verlag, p. 133-142.
P. Jutzi et al., "Cyclopentadienyl compounds with nitrogen donors in the side-chain," *Journal of Organometallic Chemistry*, vol. 500, p. 175-185 (1995).
G. Kraus et al., "A Method for Characterization of Long-Chain Branched Polymers by GPC and Intrinsic Viscosity," *J. Polymer Sci.: Symposium* No. 43, p. 329-343 (1973).
M. Pollard et al., "Observation of Chain Branching in Polyethylene in the Solid State and Melt via $^{13}C$ NMR Spectroscopy and Melt NMR Relaxation Time Measurements," *Macromolecules*, vol. 37(3), p. 813,825 (2004).
R. Koopmans, "Extrudate Swell of High Density Polyethylene. Part I: Aspects of Molecular Structure and Rheological Characterization Methods," *Polymer Engineering and Science*, vol. 32(23), p. 1741-1749 (1992).
J. Vega et al., "Small-Amplitude Oscillatory Shear Flow Measurements as a Tool To Detect Very Low Amounts of Long Chain Branching in Polyethylenes," *Macromolecules*, vol. 31(11), p. 3639-3647 (1998).
P. Wood-Adams et al., "Effect of Molecular Structure on the Linear Viscoelastic Behavior of Polyethylene," *Macromolecules*, vol. 33(20), p. 7489-7499 (2000).
C. Piel et al., "Structure-Property Relationships of Linear and Long-Chain Branched Metallocene High-Density Polyethylenes Characterized by Shear Rheology and SEC-MALLS," *Macromolecular Chemistry and Physics*, vol. 207, p. 26-38 (2006).
W. Kaminsky et al., "Polymerization of Ethene and Longer Chained Olefins by Metallocene Catalysis," *Macromol. Symp.*, vol. 226, p. 25-34 (2005).
K. Klimke et al., "Optimisation and Application of Polyolefin Branch Quantification by Melt-State $^{13}C$ NMR Spectroscopy," *Macromol. Chem. Phys.*, vol. 207, p. 382-395 (2006).
S. Bin Wadud et al., "Shear and extensional rheology of sparsely branched metallocene-catalyzed polyethylenes," *J. Rheol.*, vol. 44(5), p. 1151-1167 (2000).
D. Yan et al., "Effect of long chain branching on rheological properties of metallocene polyethylene," *Polymer*, vol. 40, p. 1737-1744 (1999).
F. Stadler et al., "Influence of type and content of very long comonomers on long-chain branching of ethene-/α-olefin copolymers," *Macromolecules*, vol. 39(4), p. 1474-1500 (2006).
J. Janzen et al., "Diagnosing long-chain branching in polyethylenes," *Journal of Molecular Structure*, vol. 485-486, p. 569-584 (1999).
C. Gabriel et al., "Analytical and rheological characterization of long-chain branched metallocene-catalyzed ethylene homopolymers," *Polymer*, vol. 43, p. 6383-6390 (2002).
B. Zimm et al.,"The Dimension of Chain Molecules Containing Branches and Rings," *The Journal of Chemical Physics*, vol. 17(12), p. 1301-1314 (1949).
Barth, H. G., & Mays, J. W. (1991). *Modern methods of polymer characterization*. Chemical analysis, v. 113. New York: Wiley.
N. Hadjichristidis et al., "Well-Defined, Model Long Chain Branched Polyethylene. 1. Synthesis and Characterization," *Macromolecules*, vol. 33(7), p. 2424-2436 (2000).
E. Kokko et al., "Long-Chain Branched Polyethylene via Metallocene-Catalysis: Comparison of Catalysts," Contribution in *Organometallic Catalysts and Olefin Polymerization* by R. Blom et al., p. 335-345 (2001).
J. Stange et al., "Rheological behavior of blends from a linear and a long-chain branched polypropylene," *J. Rheol.*, vol. 49(5), p. 1059-1079 (2005).
H. Münstedt et al., "Rheological measuring techniques and their relevance for the molecular characterization of polymers," *J. Non-Newtonian Fluid Mech.*, vol. 128, p. 1-8 (2005).
T. McLeish et al., "Molecular constitutive equations for a class of branched polymer: The pom-pom polymer," *J. Rheol.*, vol. 42(1), p. 81-110 (1998).
I. Vittorias et al., "Detection and quantification of industrial polyethylene branching topologies via Fourier-transform rheology, NMR and simulation using the Pom-pom model," *Rheol. Acta*, vol. 46, p. 321-340 (2007).
E. van Ruymbeke et al., "A sensitive method to detect very low levels of long chain branching from the molar mass distribution and linear viscoelastic response," *J. Rheol.*, vol. 49(6), p. 1-18 (2005).
S. Trinkle et al., "Van Gurp-Palmen Plot II-classification of long chain branched polymers by their topology," *Rheol Acta*; vol. 41, p. 103-113 (2002).
D. Lohse et al., "Well-Defined, Model Long Chain Branched Polyethylene. 2. Melt Rheological Behavior," *Macromolecules*, vol. 35(8), p. 3066-3075 (2002).
C. Gabriel et al., "Influence of long-chain branches in polyethylenes on linear viscoelastic flow properties in shear," *Rheol Acta*, vol. 41, p. 232-244 (2002).

B. Bersted et al., "Prediction of Rheological Behavior of Branched Polyethylene from Molecular Structure," *Journal of Applied Polymer Science*, vol. 26, p. 1001-1014 (1981).

B. Bersted, "On the Effects of Very Low Levels of Long Chain Branching on Rheological Behavior in Polyethylene," *J. of Applied Polymer Science*, vol. 30, p. 3751-3765 (1985).

H. Park et al., "Influence of long-chain branching on time-pressure and time-temperature shift factors for polystyrene and polyethylene," *Rheol Acta*, vol. 46, p. 153-159 (2006).

C. Gabriel et al., "Influence of molecular structure on rheological properties of polyethylenes," *Rheol Acta*, vol. 37, p. 7-20 (1998).

G. Schlatter et al., "Fourier Transform Rheology of Branched Polyethylene: Experiments and Models for Assessing the Macromolecular Architecture," *Macromolecules*, vol. 38, p. 6492-6544 (2005).

H. Münstedt et al., "Influence of molecular structure on rheological properties of polyethylenes; Part II. Elongational behavior," *Rheol Acta*, vol. 37, p. 21-29 (1998).

I. Vittorias et al., "Detection of Long-Chain Branching in Polylolefins via Fourier-Transform Rheology and Finite Element Simulations," *Macromol. Mat. Eng.*, p. 115-120 (2007).

G. Georgiou, "Stick-Slip Instability," *Polymer Processing Instabilities* edited by S. Hatzikiriakos & S. Migler, Dekker, NY, p. 161-206 (2005).

S. Wang et al., "Exploring molecular origins of sharkskin, partial slip, and slope change in flow curves of linear low density polyethylene," *J. Rheol.*, vol. 40(5), p. 875-898 (1996).

S. Wang et al., Stick-slip transition in capillary flow of linear polyethylene: 3. Surface conditions, *Rheol Acta*, vol. 36, p. 128-134 (1997).

* cited by examiner

COPOLYMERS OF ETHYLENE WITH α-OLEFINS

This application is the U.S. national phase of International Application PCT/EP2003/014437, filed Dec. 18, 2003, claiming priority to German Patent Application 10261252.8 filed Dec. 20, 2002, and the benefit under 35 U.S.C. 119(e) of U.S. Provisional Application No. 60/451,836, filed Mar. 4, 2003; the disclosures of International Application PCT/EP2003/014437, German Patent Application 10261252.8 and U.S. Provisional Application No. 60/451,836, each as filed, are incorporated herein by reference.

The present invention relates to copolymers of ethylene with α-olefins which have a molar mass distribution $M_w/M_n$ of from 1 to 8, a density of from 0.85 to 0.94 g/cm$^3$, a molar mass $M_n$ of from 10 000 g/mol to 4 000 000 g/mol and a CDBI of less than 50% and in which the side chain branching of the maxima of the individual peaks of the side chain branching distribution is in each case greater than 5 CH$_3$/1 000 carbon atoms, to a process for preparing them and to fibers, moldings, films or polymer mixtures in which these copolymers are present.

Copolymers of ethylene with higher α-olefins such as propene, 1-butene, 1-pentene, 1-hexene or 1-octene, known as LLDPE (linear low density polyethylene), can be prepared, for example, using classical Ziegler-Natta catalysts based on titanium or else by means of metallocenes. Since these ethylene copolymers do not consist of many equal-length chains but have a molar mass distribution comprising relatively long and relatively short polymer chains, the incorporation of the comonomer into the chains of various lengths may be the same or different. The number of side chains formed by incorporation of the comonomer and their distribution, known as the short chain branching distribution SCBD, is very different when different catalyst systems are used. The number and distribution of the side chains has a critical influence on the crystallization behavior of the ethylene copolymers. While the flow properties and thus the processing of these ethylene copolymers depends mainly on their molar mass and molar mass distribution, the mechanical properties are highly dependent on the short chain branching distribution. The short chain branching distribution also places a role in particular processing methods, e.g. in film extrusion where the crystallization properties of the ethylene copolymers during cooling of the extruded film is an important factor in determining the speed with which a film can be extruded and the resulting film quality.

There are various methods of determining the short chain branching distribution. One method is the "analytical temperature rising elution fractionation technique" (TREF). Here, the polymer is slowly crystallized from a polymer solution onto an inert support material by cooling and Is subsequently eluted at various temperatures. The concentration of polymer In the fractions obtained at various temperatures is measured by means of infrared spectroscopy. At low temperatures, molecules having a large number of side chains are eluted. As the temperature increases, the less branched polymer fractions are also eluted. The concentration of the polymer solutions obtained is plotted against the elution temperature so as to obtain the short chain branching distribution. The TREF result can also be calibrated by means of preparatively isolated polyethylene fractions having a defined number of short chain branches. The number of the side chains is usually reported as methyl groups per 1 000 carbon atoms of the polymer chains (CH$_3$/1 000C) and thus includes the end groups and any long chain branches formed in the polymerization. The TREF method is described, for example, in Wild, Advances in Polymer Science, 98, p. 1-47, 57 p. 153, 1992. From the TREF, it is possible to determine, for example, the CDBI (composition distribution breadth index), which is a measure of the breadth of the distribution of the composition. This is described, for example, in WO 93/03093. The CDBI is defined as the percent by weight of the copolymer molecules having a comonomer content of ±25% of the mean molar total comonomer content.

A new method of determining the short chain branching distribution, namely Crystaf®, has recently been developed, since the TREF method is very time-consuming. Here, the short chain branching is determined in a single step during the process of crystallization from the polymer solution. The polymer solution is stirred, slowly cooled and a sample of the solution is taken at particular temperatures. These samples contain the polymer fractions which have not yet crystallized and their concentration is determined by means of Infrared spectroscopy. Since the samples are taken during the crystallization process, a cumulative short chain branching distribution is obtained. Subtraction enables a short chain branching distribution similar to that obtained from TREF to be obtained. Apart from rapid measurement of data, the Crystaf® method offers the additional advantage that the soluble or uncrystallizable polymer components can also be determined by this means (Monrabal B.; Crystallization analysis fractionation, a new technique for the analysis of branching distribution in polyolefines; J. appl. Polym. Sci. 1994;52;491-9).

Ziegler-Natta catalysts give LLDPE having a broad or bimodal short chain branching distribution and a relatively broad mean molar mass distribution $M_w/M_n$ which is usually greater than 5, where $M_n$ is the number average molar mass and $M_W$ is the weight average molar mass. The side chain branching is usually more pronounced in the polymer chains having a relatively low molar mass than in those having higher molar masses. Furthermore, these copolymers contain a high molecular weight polymer fraction having an extremely small proportion of side chain branches of less than 4CH$_3$/1 000 carbon atoms.

In contrast, use of metallocene catalysts in the polymerization usually gives ethylene copolymers having a narrow molar mass distribution and a CDBI of >50%. These LLDPEs have particularly advantageous mechanical properties. The short chain branching distribution is monomodal. Copolymerization with higher α-olefins often leads to a reduced molecular weight. In general, chain termination becomes increasingly favored at higher comonomer concentrations and the molecular weight is thus reduced (U.S. Pat. No. 5,625,016 states that $M_n$ is smaller than about 50 000). The low molecular weight copolymers can lead, firstly, to deposits in the reactor during the polymerization and, secondly, to undesirable product properties such as sticky surfaces. LLDPEs having a high molecular weight and a high comonomer content are difficult to produce.

WO 01/92346 discloses cyclopentadienyl complexes of groups 4-6 of the Periodic Table of the Elements in which a dihydrocarbyl-Y group, where Y is an element of group 14 of the Periodic Table of the Elements bearing particular Lewis bases, is bound to the cyclopentadienyl system.

WO-A-98/44011 describes ethylene copolymers with at least one alpha-olefin having at least 5 carbon atoms which have a melt index MI of from 0.1 to 15, a CDBI of at least 70%, a density of from 0.91 to 0.93 g/ml, a haze value of less than 20%, a melt index ratio MIR of from 35 to 80, a mean modulus of from 20 000 to 60 000 psi and a defined ratio of modulus to dart impact strength. Furthermore, the resulting polymers are said to have essentially no unsaturated end groups.

WO-A-93/12151 describes ethylene copolymers with alpha-olefins having at least 10 carbon atoms which have a density of from 0.85 to 0.95 g/cm$^3$, a mean molecular weight $M_W$ of from 30 000 to 1 000 000 dalton and a molecular weight distribution in the range from 2 to 4.

It has now been found that ethylene copolymers having an at least bimodal short chain branching distribution and at the same time a narrow molar mass distribution and a particularly good dart drop impact strength are obtained when the polymerization is carried out using particular chromium catalysts.

We have accordingly found copolymers of ethylene with α-olefins which have a molar mass distribution $M_W/M_n$ of from 1 to 8, a density of from 0.85 to 0.94 g/cm$^3$, a molar mass $M_n$ of from 10 000 g/mol to 4 000 000 g/mol, a CDBI of less than 50% and in which the side chain branching of the maxima of the individual peaks of the short chain branching distribution is in each case greater than 5 CH$_3$/1 000 carbon atoms.

Furthermore, we have found a process for preparing the ethylene copolymers of the present invention, which comprises polymerizing ethylene with α-olefins in the presence of the following components:

A) at least one monocyclopentadienyl complex comprising the structural feature of the formula (Cp-Z-A)Cr (I), where the variables have the following meanings:
CP-Z-A is a ligand of the formula (II)

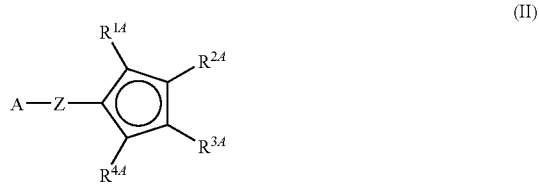

(II)

where
$R^{1A}$-$R^{4A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{11A}{}_2$, $N(SiR^{11A}{}_3)_2$, $OR^{11A}$, $OSiR^{11A}{}_3$, $SiR^{11A}{}_3$, $BR^{11A}{}_2$, where the organic radicals $R^{1A}$-$R^{4A}$ may also be substituted by halogens and where at least two of the vicinal radicals $R^{1A}$-$R^{4A}$ are joined to form a five- or six-membered ring, and/or two vicinal radicals $R^{1A}$-$R^{4A}$ are joined to form a heterocycle which contains at least one atom from the group consisting of N, P, O and S, Z is a bridge between A and Cp having the formula

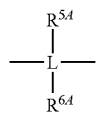

where
L is carbon or silicon, preferably carbon,
$R^{5A}$,$R^{6A}$ are each hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{11A}{}_3$, where the organic radicals $R^{5A}$ and $R^{6A}$ may also be substituted by halogens and $R^{5A}$ and $R^{6A}$ may also be joined to form a five- or six-membered ring, A is

(III)

where
$E^{1A}$-$E^{4A}$ are each carbon or nitrogen,
$R^{7A}$-$R^{10A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{11A}{}_3$, where the organic radicals $R^{7A}$-$R^{10A}$ may also bear halogens or nitrogen or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{11A}{}_3$ as substituents and two vicinal radicals $R^{7A}$-$R^{10A}$ or $R^{7A}$ and Z may also be joined to form a five- or six-membered ring,
$R^{11A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^{11A}$ may also be joined to form a five- or six-membered ring and
p is 0 when $E^{1A}$-$E^{4A}$ is nitrogen and is 1 when $E^{1A}$-$E^{4A}$ is carbon, B) optionally an organic or inorganic support,
C) optionally one or more activating compounds and
D) optionally one or more metal compounds containing a metal of group 1, 2 or 13 of the Periodic Table.

Furthermore, we have found polymer mixtures in which at least one copolymer of ethylene with $C_3$-$C_{12}$-α-Olefins according to the present invention is present and also fibers, films and moldings in which the copolymers of ethylene with $C_3$-$C_{12}$-α-olefins according to the present invention are present as significant component.

We have also found the use of the copolymers of ethylene with $C_3$-$C_{12}$-α-olefins of the present invention for producing fibers, films and moldings.

Preferred copolymers of ethylene with α-olefins are those which have a molar mass distribution $M_W/M_n$ of from 1 to 8, a density of from 0.85 to 0.94 g/cm$^3$, a molar mass $M_n$ of from 10 000 g/mol to 4 000 000 g/mol and an at least bimodal short chain branching distribution and in which the side chain branching of the maxima of the individual peaks of the short chain branching distribution is in each case greater than 5 CH$_3$/1 000 carbon atoms.

Particular preference is given to copolymers of ethylene with α-olefins which have a molar mass distribution $M_W/M_n$ of from 1 to 8, a density of from 0.85 to 0.94 g/cm$^3$, a molar mass $M_n$ of from 10 000 g/mol to 4 000 000 g/mol, a CDBI of less than 50% and an at least bimodal short chain branching distribution and in which the side chain branching of the maxima of the individual peaks of the short chain branching distribution is in each case greater than 5 CH$_3$/1 000 carbon atoms.

The copolymer of ethylene with $C_3$-$C_{12}$-α-olefins of the present invention has a molar mass distribution $M_w/M_n$ of from 1 to 8, preferably from 1.5 to 5 and particularly preferably from 2 to 3.5. Its density is In the range from 0.85 to 0.94 g/cm$^3$, preferably from 0.86 to 0.93 g/cm$^3$ and particularly preferably from 0.87 to 0.91 g/cm$^3$. The molar mass $M_n$ of the ethylene copolymers of the present invention is in the range from 10 000 g/mol to 4 000 000 g/mol, preferably from 50 000 g/mol to 1 000 000 g/mol and particularly preferably from 100 000 g/mol to 400 000 g/mol.

For the purposes of the present patent application, a monomodal short chain branching distribution means that the short chain branching distribution determined by the Crystaf® method displays a single maximum. A bimodal short chain branching distribution means, for the purposes of the present patent application, that the short chain branching distribution determined by the Crystaf® method has at least two points of inflection on a flank of a maximum. For the purposes of the present patent application, an at least bimodal short chain branching distribution is one which may be bimodal, trimodal, etc., or multimodal. The short chain branching distribution is preferably bimodal or trimodal, in particular bimodal.

The side chain branching of the maxima of the individual peaks of the short chain branching distribution is in each case greater than 5 $CH_3$/1 000 carbon atoms, preferably greater than 8 $CH_3$/1 000 carbon atoms, and is preferably in the range from 10 to 80 $CH_3$/1 000 carbon atoms and particularly preferably from 15 to 60 $CH_3$/1 000 carbon atoms.

According to the present invention, the short chain branching distribution and the number of side chains is determined by means of the Crystaf® method. The elution temperatures obtained in this way are converted by means of the reference table into the number of $CH_3$ groups per 1 000 carbon atoms.

The molar mass distribution within the short chain branching distribution is preferably such that the fractions which form the peak having the highest number of $CH_3$/1 000 carbon atoms have a mean molar mass which is equal to or higher than that of the peak(s) having a lower number of $CH_3$/1 000 carbon atoms.

The peak having the highest number preferably has at least 8, preferably at least 12 and particularly preferably at least 15, $CH_3$/1 000 carbon atoms more than the peak having the smallest number of $CH_3$/1 000 carbon atoms.

The ethylene copolymer of the present invention preferably has no peak in the Crystaf® spectrum of the differential distribution above 80° C., preferentially not above 75° C. When used in film applications the ethylene copolymers therefore show increased dart drop impact values and/or tensile yield and/or Elemendorf tear resistance. When used in heat sealable films the resulting films show low sealing temperatures but excellent mechanics of seal. When used as blend compositions the resulting blends show higher clarity and permeability compared to blends with conventional ethylene copolymers.

The ethylene copolymer of the present invention preferably has at least one peak in the Crystaf® spectrum of the differential distribution in the range from 5 to 40° C. and at least one further peak in the Crystaf® spectrum of the differential distribution in the range from 25 to 80° C., preferably at least one peak in the Crystaf® spectrum of the differential distribution in the range from 8 to 30° C. and at least one further peak in the Crystaf® spectrum of the differential distribution in the range from 28 to 60° C.

The HLMFR of the ethylene copolymers of the present invention is in the range from 0.001 to 200 g/10 min, preferably from 0.1 to 50 g/10 min and especially preferable from 2 to 40 g/10 min. For the purpose of the present invention, the expression "HLMFR" refers to the "high load melt flow rate" and is determined in accordance with ISO 1133 at 190° C. under a load of 21.6 kg (190° C./21.6 kg).

The ethylene copolymers of the present invention have preferably a long chain branching (lcb) rate λ (lambda) from 0 to 0.1 lcb/1000 carbon atoms, preferably from 0.001 to 0.09 lcb/1000 carbon atoms as measured by light scattering as described in ACS Series 521, 1993, Chromatography of Polymers, Ed. Theodore Provder; Simon Pang and Alfred Rudin: Size-Exclusion Chromatographic Assessment of Long-Chain Branch Frequency in Polyethylenes, page 254-269. Films made with these ethylene copolymers therefore show high bubble stability during film processing.

The ethylene copolymers of the present invention have preferably a high vinyl group content. The vinyl group content is preferably higher than 0.05 vinyl groups/1000 carbon atoms, preferably from 0.1 to 1 vinyl groups/1000 carbon atoms and preferentially from 0.15 to 0.5 vinyl groups/1000 carbon atoms. Vinyl groups in this context refers to vinyl groups only and does not for example include vinylidene groups. The ethylene copolymers of the present invention have preferably a vinyliden group content/1000 carbon atoms, which is higher than 0.1 vinyliden groups/1000 carbon atoms, preferably from 0.1 to 1.5 vinyliden groups/1000 carbon atoms and preferentially from 0.15 to 0.8 vinyliden groups/1000 carbon atoms. The total of vinyl and vinyliden groups is preferably higher than 0.2 groups/1000 carbon atoms, preferably from 0.2 to 2 groups/1000 carbon atoms and preferentially from 0.3 to 1 groups/1000 carbon atoms. Vinyl groups usually are associated with a polymer chain termination after an ethylene insertion, whereas vinylidene groups are thought to occur if the polymer chain is terminated after comonomer insertion, like for example hexene insertion. Vinyliden and vinyl groups can be reacted with a functionalisation reagent or used for cross linking. The ethylene copolymers of the present invention are therefore very suitable for grafting, cross linking and functionalisation.

In a preferred embodiment of the present invention, the copolymer has an index of the breadth of the composition distribution of the comonomer of less than 50%, in particular from 5 to 45% and particularly preferably from 20 to 30%.

As comonomers which may be present, either individually or in admixture with one another, in addition to ethylene in the copolymer of the present invention, it is possible to use all α-olefins having from 3 to 12 carbon atoms, e.g. propene, 1-butene, 1-pentene, 1-hexene, 4-methyl-1-pentene, 1-heptene, 1-octene and 1-decene. The ethylene copolymer preferably contains, as comonomer units, copolymerized α-olefins having from 3 to 9 carbon atoms, e.g. butene, pentene, hexene, 4-methylpentene or octene. Particular preference is given to using α-olefins selected from the group consisting of propene, 1butene, 1-hexene and 1-octene. The comonomers are generally present in copolymerized form in the ethylene copolymer of the present invention in amounts of from 1 to 40% by weight, preferably from 2 to 30% by weight and in particular from 2 to 20% by weight, in each case based on the ethylene copolymer.

The ethylene copolymers can, in particular, be prepared by means of the above-described novel process using the substituted monoindenylchromium complexes of the formula I.

The monocyclopentadienyl complexes A) used in the process of the present invention comprise the structural element of the formula $(Cp\text{-}Z\text{-}A)_m Cr$ (I), where the variables are as defined above. The further ligands can therefore be bound to the metal atom Cr. The number of further ligands depends, for example, on the oxidation state of the metal atom. Possible further ligands do not include further cyclopentadienyl systems. Suitable further ligands are monoanionic and dianionic ligands as are described, for example, for X. In addition, Lewis bases such as amines, ethers, ketones, aldehydes, esters, sulfides or phosphines can also be bound to the metal center Cr.

The polymerization behavior of the metal complexes can likewise be influenced by variation of the substituents $R^{1A}$-$R^{4A}$. The number and type of substituents can influence the ability of the olefins to be polymerized to gain access to the metal atom M. This makes it possible to modify the activity and selectivity of the catalyst In respect of various monomers, in particular bulky monomers. Since the substituents can also influence the rate of termination reactions of the growing polymer chain, the molecular weight of the polymers formed can also be altered in this way. The chemical structure of the substituents $R^{1A}$ to $R^{4A}$ can therefore be varied within a wide range in order to achieve the desired results and to obtain a tailored catalyst system with the proviso that at least two of the vicinal radicals $R^{1A}$-$R^{4A}$ are joined to form a five- or six-membered ring, and/or two vicinal radicals $R^{1A}$-$R^{4A}$ are Joined to form a heterocycle which contains at least one atom from the group consisting of N, P, O and S. Possible carboorganic substituents $R^{1A}$-$R^{4A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl, which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where the organic radicals $R^{1A}$-$R^{4A}$ may also be substituted by halogens such as fluorine, chlorine or bromine. Furthermore, $R^{1A}$-$R^{4A}$ may also be amino or alkoxy, for example dimethylamino, N-pyrrolidinyl, picolinyl, methoxy, ethoxy or isopropoxy. In organosilicon substituents $SiR^{11A}_3$, $R^{11A}$ may be the same carboorganic radicals as described in more detail in this paragraph for $R^{1A}$-$R^{4A}$, with two $R^{11A}$ also being able to be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl. These $SiR^{11A}_3$ radicals may also be bound to the cyclopentadienyl skeleton via an oxygen or nitrogen atom, for example trimethylsilyloxy, triethylsilyloxy, butyldimethylsilyloxy, tributylsilyloxy or tri-tert-butylsilyloxy. Preferred radicals $R^{1A}$-$R^{4A}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or ortho-dichloro-substituted phenyls, trialkyl or trichloro-substituted phenyls, naphthyl, biphenyl and anthranyl. As organosilicon substituents, particular preference is given to trialkylsilyl groups having from 1 to 10 carbon atoms in the alkyl radical, in particular trimethylsilyl groups.

At least two of the vicinal radicals $R^{1A}$-$R^{4A}$ are joined to form a five- or six-membered ring, and/or two vicinal radicals $R^{1A}$-$R^{4A}$ are joined to form a heterocycle which contains at least one atom from the group consisting of N, P, O and S. Two vicinal radicals $R^{1A}$-$R^{4A}$ can, for example, in each case together with the carbon atoms bearing them, form a heterocycle, preferably a heteroaromatic, which contains at least one atom from the group consisting of nitrogen, phosphorus, oxygen and sulfur, particularly preferably nitrogen and/or sulfur. Preference is given to heterocycles and heteroaromatics having a ring size of 5 or 6 ring atoms. Examples of 5-membered heterocycles, which may contain from one to three nitrogen atoms and/or a sulfur or oxygen atom as ring atoms in addition to carbon atoms, are 1,2-dihydrofuran, furan, thiophene, pyrrole, isoxazole, 3-isothiazole, pyrazole, oxazole, thiazole, imidazole. Examples of 6-membered heteroaryl groups, which may contain from one to four nitrogen atoms and/or a phosphorus atom, are pyridine, phosphabenzene, pyridazine, pyrimidine, pyrazine, 1,3,5-triazine, 1,2, 4triazine and 1,2,3-triazine. The 5- and 6-membered heterocycles may also be substituted by $C_1$-$C_{10}$-alkyl, $C_6$-$C_{10}$-aryl, alkylaryl having from 1 to 10 carbon atoms In the alkyl part and 6-10 carbon atoms in the aryl part, trialkylsilyl or halogens such as fluorine, chlorine or bromine, dialkylamide, alkylarylamide, diarylamide, alkoxy or aryloxy or be fused with one or more aromatics or heteroaromatics. Examples of the benzo-fused 5-membered heteroaryl groups are indole, indazole, benzofuran, benzothiophene, benzothiazole, benzoxazole and benzimidazole. Examples of benzo-fused 6-membered heteroaryl groups are chroman, benzopyran, quinoline, isoquinoline, cinnoline, phthalazine, quinazoline, quinoxaline, 1,10-phenanthroline and quinolizine. Naming and numbering of the heterocycles has been taken from Lettau, Chemie der Heterocyclen, 1st edition, VEB, Weinheim 1979. The are preferably fused with the cyclopentadienyl skeleton via a C—C double bond of the heterocycle/heteroaromatic. Heterocycles/heteroaromatics containing a heteroatom are preferably 2,3- or b-fused.

Examples of cyclopentadienyl systems Cp having a fused heterocycle are thiapentalene, 2-methylthiapentalene, 2-ethylthiapentalene, 2-isopropylthiapentalene, 2-n-butylthiapentalene, 2-tert-butylthiapentalene, 2-trimethylsilylthiapentalene, 2-phenylthiapentalene, 2-naphthylthiapentalene, 3-methylthiopentalene, 4-phenyl-2,6dimethyl-1-thiapentalene, 4-phenyl-2,6-diethyl-1-thiapentalene, 4-phenyl-2,6-diisopropyl-1-thiapentalene, 4-phenyl-2,6-di-n-butyl-1-thiapentalene, 4-phenyl-2,6-di(trimethylsilyl)-1-thiapentalene, azapentalene, 2-methylazapentalene, 2-ethylazapentalene, 2-isopropylazapentalene, 2-n-butylazapentalene, 2-trimethylsilylazapentalene, 2-phenylazapentalene, 2-naphthylazapentalene, 1-phenyl-2,5-dimethyl-1-azapentalene, 1-phenyl-2,5-diethyl-1-azapentalene, 1-phenyl-2,5-di-tert-butyl-1-azapentalene, 1-phenyl-2,5-di(trimethysilyl)-1-azapentalene, 1-tert-butyl-2,5-dimethyl-1-azapentalene, oxapentalene, phosphapentalene, 1-phenyl-2,5-dimethyl-1-phosphapentalene, 1-phenyl-2,5-diethyl-1-phosphapentalene, 1-phenyl-2,5-di-n-butyl-1-phosphapentalene, 1-phenyl-2,5-di-tert-butyl-1-phosphapentalene, 1-phenyl-2,5-di (trimethylsilyl)-1-phosphapentalene, 1-methyl-2,5-dimethyl-1-phosphapentalene, 1-tert-butyl-2,5-dimethyl-1-phosphapentalene, 7-cyclopenta[1,2]thieno[3,4]cyclopentadiene or 7-cyclopenta[1,2]pyrrolo[3,4]cyclopentadiene.

In further preferred cyclopentadienyl systems Cp, the four radicals $R^{1A}$-$R^{4A}$, i.e. two pairs of vicinal radicals, form two heterocycles, in particular heteroaromatics. The heterocyclic systems are the same as those described in more detail above. Examples of cyclopentadienyl systems Cp having two fused-on heterocycles are 7-cyclopentadithiophene, 7-cyclopentadipyrrole or 7-cyclopentadiphosphole.

The synthesis of such cyclopentadienyl systems having a fused-on heterocycle is described, for example, in the abovementioned WO 98/22486. In "metalorganic catalysts for synthesis and polymerization", Springer Verlag 1999, p. 150 ff, Ewen et al. describe further syntheses of these cyclopentadienyl systems.

Preference is also given to compounds in which two vicinal radicals $R^{1A}$-$R^{4A}$, in particular $R^{1A}$ together with $R^{2A}$ and/or $R^{3A}$ together with $R^{4A}$, form a fused ring system, in particular a $C_6$ ring system, particularly preferably an aromatic $C_6$ ring system, i.e. together with the cyclopentadienyl $C_5$ ring form, for example, an unsubstituted or substituted indenyl, benzindenyl, phenanthrenyl, fluorenyl or tetrahydroindenyl system, e.g. indenyl, 2-methylindenyl, 2-ethylindenyl, 2-isopropylindenyl, 3-methylindenyl, benzindenyl or 2-methylbenzindenyl. In particular, $R^{1A}$ and $R^{2A}$ together with the cyclopentadienyl system form a substituted or unsubstituted indenyl system.

The fused ring system may bear a further $C_1$-$C_{20}$-alkyl groups, $C_2$-$C_{20}$-alkenyl groups, $C_6$-$C_{20}$-aryl groups, alkylaryl groups having from 1 to 10 carbon atoms In the alkyl part and 6-20 carbon atoms in the aryl part, $NR^{11A}_2$, $N(SiR^{11A}_3)_2$, $OR^{11A}$, $OSiR^{11A}_3$ or $SiR^{11A}_3$, e.g. 4-methylindenyl, 4-ethylindenyl, 4-isopropylindenyl, 5-methylindenyl, 4-phenylindenyl, 5-methyl-4-phenylindenyl, 2-methyl-4-phenylindenyl or 4-naphthylindenyl.

As in the case of metallocenes, the monocyclopentadienyl complexes A) may be chiral. Thus, one of the substituents $R^{1A}$-$R^{4A}$ of the cyclopentadienyl skeleton can have one or more chiral centers, or else the cyclopentadienyl system Cp can itself be enantiotopic, so that chirality is induced only when the cyclopentadienyl system is bound to the transition metal M (for formalisms regarding chirality in cyclopentadienyl compounds, cf. R. Halterman, Chem. Rev. 92, (1992), 965-994).

Possible carboorganic substituents $R^{5A}$-$R^{6A}$ on the link Z are, for example, the following: hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-,2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where the organic radicals $R^{5A}$ and $R^{6A}$ may also be joined to form a 5- or 6-membered ring or may be substituted by halogens, e.g. fluorine, chlorine or bromine, or alkyl or aryl.

In organosilicon substituents $SiR^{11A}_3$, possible radicals $R^{11A}$ are the same radicals as mentioned in more detail above, with it also being possible for two $R^{11A}$ to be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl.

The radicals $R^{5A}$ and $R^{6A}$ may be identical or different. Preferred radicals $R^{5A}$ and $R^{6A}$ are hydrogen, methyl, ethyl, n-propyl, isopropyl, n-butyl, isobutyl, tert-butyl, n-pentyl, n-hexyl, n-heptyl, n-octyl, benzyl, phenyl, ortho-dialkyl- or ortho-dichloro-substituted phenyls, trialkyl- or trichloro-substituted phenyls, naphthyl, biphenyl and anthranyl.

The bridge Z between the cyclopentadienyl system Cp and the heteroaromatic A is an organic, preferably divalent bridge. Z is preferably a group $CR^{5A}R^{6A}$. Z is very particularly preferably bound both to the fused heterocycle or fused-on aromatic and to the cyclopentadienyl skeleton. Thus, if the heterocycle or aromatic is fused on in the 2,3 position of the cyclopentadienyl skeleton, Z is preferably located in the 1 or 4 position of the cyclopentadienyl skeleton.

A is an unsubstituted, substituted or fused heteroaromatic, six-membered ring system having 1, 2, 3, 4 or 5 nitrogen atoms in the heteroaromatic part which is bound to Z, in particular 2-pyridyl or 2-quinolyl. Examples of 6-membered heteroaryl groups, which can contain from one to five nitrogen atoms, are 2-pyridinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 6-membered heteroaryl groups may also bear $C_1$-$C_{10}$-alkyl groups, $C_6$-$C_{10}$-aryl groups, alkylaryl groups having from 1 to 10 carbon atoms in the alkyl part and 6-10 carbon atoms in the aryl part, trialkylsilyl groups or halogens such as fluorine, chlorine or bromine as substituents or be fused with one or more aromatics or heteroaromatics. Examples of benzo-fused 6-membered heteroaryl groups are 2-quinolyl, 3-cinnolyl, 2-quinazolyl, 4-quinazolyl, 2-quinoxalyl, 1-phenanthridyl and 1-phenazyl.

A can bind to the metal M either intermolecularly or intramolecularly. A is preferably bound intramolecularly to M. The synthesis to bind A to the cyclopentadienyl ring can be carried out, for example, by a method analogous to that of M. Enders et al. in Chem. Ber. (1996), 129, 459-463, or P. Jutzi and U. Siemeling in J. Orgmet Chem. (1995), 500, 175-185.

Examples of possible carboorganic substituents $R^{7A}$-$R^{10A}$ in A are the following: hydrogen, $C_1$-$C_{20}$-alkyl which may be linear or branched, e.g. methyl, ethyl, n-propyl, Isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-,2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where two vicinal radicals $R^{7A}$ to $R^{10A}$ may also be bound to form a 5- or 6-membered ring or may be substituted by halogens, e.g. fluorine, chlorine or bromine, or alkyl or aryl. $R^{7A}$-$R^{10A}$ are preferably each hydrogen, methyl, ethyl, n-propyl, isopropyl, n-butyl, isobutyl, tert-butyl, n-pentyl, n-hexyl, n-heptyl, n-octyl, benzyl or phenyl. In organosilicon substituents $SiR^{11A}_3$, possible radicals $R^{11A}$ are the same radicals as mentioned in more detail above, with two $R^{11A}$ also being able to be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl.

In particular, 0 or 1 $E^{1A}$-$E^{4A}$ in A is nitrogen and the others are carbon. A is particularly preferably 2-pyridyl, 6-methyl-2-pyridyl, 4-methyl-2-pyridyl, 5-methyl-2-pyridyl, 5-ethyl-2-pyridyl, 4,6-dimethyl-2-pyridyl, 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethyl-2- pyrazinyl, 3,5,6-trimethyl-2-pyrazinyl, 2-quinolyl, 4-methyl-2-quinolyl, 6-methyl-2-quinolyl, 7-methyl-2-quinolyl, 2-quinoxalyl or 3-methyl-2-quinoxalyl.

The chromium is particularly preferably present in one of the oxidation states 2, 3 and 4, In particular 3. The chromium complexes can be obtained in a simple manner by reacting the appropriate metal salts, e.g. chromium chlorides, with the ligand anion (e.g. using a method analogous to the examples in DE 197 10615).

In the process of the present invention, preference is given to monocyclopentadienyl complexes A) of the formula (Cp-Z-A)CrX$_k$ (Ian), where the variables Cp, Z and A are as defined above and their preferred embodiments are also preferred here and:

X are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, alkylaryl having 1-10 carbon atoms in the alkyl part and 6-20 carbon atoms in the aryl part, $NR^1R^2$, $OR^1$, $SR^1$, $SO_3R^1$, $OC(O)R^1$, CN, SCN, β-diketonate, CO, $BF_4^-$, $PF_6^-$ or a bulky noncoordinating anion, $R^1$-$R^2$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^3_3$, where the organic radicals $R^1$-$R^2$ may also be substituted by halogens or nitrogen- and oxygen-containing groups and two radicals $R^1$-$R^2$ may also be joined to form a five- or six-membered ring, $R^3$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two radicals $R^3$ may also be joined to form a five- or six-membered ring and k is 1, 2 or 3.

The embodiments and preferred embodiments of Cp, Z and A described above also apply individually and in combination to these preferred monocyclopentadienyl complexes A).

The ligands X can result, for example, from the choice of the corresponding starting chromium compounds which are used for the synthesis of the monocyclopentadienyl complexes, but can also be varied afterwards. Suitable ligands X are, in particular, the halogens fluorine, chlorine, bromine or iodine, in particular chlorine. Alkyl radicals such as methyl, ethyl, propyl, butyl, vinyl, allyl, phenyl or benzyl are also advantageous ligands X. Further possible ligands X are, purely by way of example and not in any way exhaustively, trifluoroacetate, $BF_4^-$, $PF_6^-$ and weakly coordinating or non-coordinating anions (cf., for example, Strauss in Chem. Rev. 1993, 93, 927-942) such as $B(C_6F_5)_4^-$.

Amides, alkoxides, sulfonates, carboxylates and β-diketonates are also particularly suitable ligands X. Variation of the radicals $R^1$ and $R^2$ enables, for example, physical properties such as solubility to be finely adjusted. Possible carboorganic substituents $R^1$-$R^2$ are, for example, the following: $C_1$-$C_{20}$-alkyl which may be linear or branched, for example methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and have an internal or terminal double bond, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N- or O-containing radicals, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6-, or 3,4,5-trimethylphenyl, 2-methoxyphenyl, 2-N,N-dimethylaminophenyl or arylalkyl which may be substituted by further alkyl groups, e.g. benzyl, o-, m-, p-methylbenzyl, 1- or 2-ethylphenyl, where $R^1$ may also be joined to $R^2$ to form a 5- or 6-membered ring and the organic radicals $R^1$-$R^2$ may also be substituted by halogens, e.g. fluorine, chlorine or bromine. In organosilicon substituents $SiR^3_3$, $R^3$ may be the same radicals as described in more detail above for $R^1$-$R^2$, with two $R^3$ also being able to be joined to form a 5- or 6-membered ring. Examples of substituents $SiR^3_3$ are trimethylsilyl, triethylsilyl, butyldimethylsilyl, tributylsilyl, trialkylsilyl, triphenylsilyl and dimethylphenylsilyl. Preference is given to using $C_1$-$C_{10}$-alkyl such as methyl, ethyl, n-propyl, n-butyl, tert-butyl, n-pentyl, n-hexyl, n-heptyl, n-octyl and also vinyl, allyl, benzyl and phenyl as radicals $R^1$ and $R^2$. Some of these substituted ligands X are very particularly preferably used since they are obtainable from cheap and readily available starting materials. In a particularly preferred embodiment X is dimethylamide, methoxide, ethoxide, isopropoxide, phenoxide, naphthoxide, triflate, p-toluenesulfonate, acetate or acetylacetonate.

The number k of the ligands X depends on the oxidation state of the chromium. The number k can therefore not be specified in general terms. The oxidation state of the transition metals M in catalytically active complexes is usually known to a person skilled in the art Chromium is very probably present in the oxidation state +3. However, it is also possible to use complexes whose oxidation state does not correspond to that of the active catalyst. Such complexes can then be appropriately reduced or oxidized by means of suitable activators. Preference is given to using chromium complexes in the oxidation state +3.

Furthermore, we have found catalyst systems for olefin polymerization comprising A') at least one monocyclopentadienyl complex A') comprising the structural feature of the formula (Cp-$CR^{5B}R^{6B}$-A)Cr (IV), where the variables have the following meanings:

Cp-$CR^{5B}R^{6B}$-A is

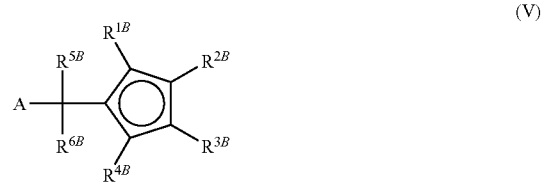

(V)

where $R^{1B}$-$R^{4B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl radical and 6-20 carbon atoms in the aryl radical, $NR^{5A}_2$, $N(SiR^{11B}_3)_2$, $OR^{11B}$, $OSiR^{11B}_3$, $SiR^{11B}_3$, $BR^{11B}_2$, where the organic radicals $R^{1B}$-$R^{4B}$ may also be substituted by halogens and two vicinal radicals $R^{1B}$-$R^{4B}$ may also be joined to form a five- or six-membered ring, $R^{5B}$, $R^{6B}$ are each hydrogen or methyl, A is

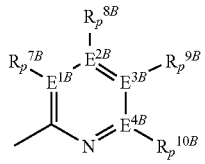

(VI)

where $E^{1B}$-$E^{4B}$ are each carbon or nitrogen, $R^{7B}$-$R^{10B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{11B}_3$, where the organic radicals $R^{7B}$-$R^{10B}$ may also bear halogens or nitrogen or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{11B}_3$ as substituents and two vicinal radicals $R^{7B}$-$R^{10B}$ may also be joined to form a five- or six-membered ring, $R^{11B}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{11B}$ may also be joined to form a five- or six-membered ring, p is 0 when $E^{1B}$-$E^{4B}$ is nitrogen and is 1 when $E^{1B}$-$E^{4B}$ is carbon, where at least one radical $R^{7B}$-$R^{10B}$ is $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{11B}_3$ and the organic radicals $R^{7B}$-$R^{10B}$ may also bear halogens or nitrogen or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{5C}_3$ as substituents and two vicinal radicals $R^{7B}$-$R^{10B}$ may also be joined to form a five- or six-membered ring or at least one $E^{1B}$-$E^{4B}$ is nitrogen, B) optionally an organic or inorganic support, C) optionally one or more activating compounds and D) optionally one or more metal compounds containing a metal of group 1, 2 or 13 of the Periodic Table.

The monocyclopentadienyl complexes A') of the present invention comprise the structural element of the formula (Cp-$CR^{5B}R^{6B}$-A)Cr (IV), where the variables are as defined above. Further ligands can therefore be bound to the metal atom M. The number of further ligands depends, for example, on the oxidation state of the metal atom. Possible further ligands do not include further cyclopentadienyl systems. Suitable further ligands are monoanionic and dianionic ligands as are described, for example, for x. In addition, Lewis bases such as amines, ethers, ketones, aldehydes, esters, sulfides or phosphines can also be bound to the metal center M.

The polymerization behavior of the metal complexes can likewise be influenced by variation of the substituents $R^{1B}$-$R^{4B}$. The number and type of substituents can influence the ability of the olefins to be polymerized to gain access to the metal atom Cr. This makes it possible to modify the activity and selectivity of the catalyst in respect of various monomers, in particular bulky monomers. Since the substituents can also influence the rate of termination reactions of the growing polymer chain, the molecular weight of the polymers formed can also be altered in this way. The chemical structure of the substituents $R^{1B}$ to $R^{4B}$ can therefore be varied within a wide range in order to achieve the desired results and to obtain a tailored catalyst system. Possible carboorganic substituents $R^{1B}$-$R^{4B}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5 to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl, which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where two $R^{1B}$ to $R^{4B}$ may also be joined to form a 5- or 6-membered ring and the organic radicals $R^{1B}$-$R^{4B}$ may also be substituted by halogens such as fluorine, chlorine or bromine. Furthermore, $R^{1B}$-$R^{4B}$ may also be amino or alkoxy, for example dimethylamino, N-pyrrolidinyl, picolinyl, methoxy, ethoxy or isopropoxy. As organosilicon substituents $SiR^{11B}_3$, $R^{11B}$ may be the same radicals as described in more detail above for the carboorganic radicals $R^{1B}$-$R^{4B}$, with two $R^{11B}$ also being able to be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl. These $SiR^{11B}_3$ radicals may also be bound to the cyclopentadienyl skeleton via an oxygen or nitrogen atom, for example trimethylsilyloxy, triethylsilyloxy, butyldimethylsilyloxy, tributylsilyloxy or tri-tert-butylsilyloxy. Preferred radicals $R^{1B}$-$R^{4B}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl or ortho-dichloro-substituted phenyls, trialkyl- or trichloro-substituted phenyls, naphthyl, biphenyl and anthranyl. As organosilicon substituents, particular preference is given to trialkylsilyl groups having from 1 to 10 carbon atoms in the alkyl radical, in particular trimethylsilyl groups.

Examples of such cyclopentadienyl systems (without the group —$CR^{5B}R^{6B}$-A, which is preferably located in the 1 position) are 3-methylcyclopentadienyl, 3-ethylcyclopentadienyl, 3-isopropyl-cyclopentadienyl, 3-tert-butylcyclopentadienyl, dialkylcyclopentadienyl such as tetrahydroindenyl, 2,4-dimethylcyclopentadienyl or 3-methyl-5-tert-butylcyclopentadienyl, trialkylcyclopentadienyl such as 2,3,5-trimethylcyclopentadienyl or tetraalkylcyclopentadienyl such as 2,3,4,5-tetramethyl-cyclopentadienyl.

Preferably at least two of the vicinal radicals $R^{1B}$-$R^{4B}$ are joined to form a five- or six-membered ring, and/or two vicinal radicals $R^{1B}$-$R^{4B}$ are joined to form a heterocycle which contains at least one atom from the group consisting of N, P, O and S.

Preference is also given to compounds in which two vicinal radicals $R^{1B}$-$R^{4B}$, in particular $R^{1B}$ together with $R^{2B}$ and/or $R^{3B}$ together with $R^{4B}$, form a five- or six-membered ring in particular a fused ring system, in particular a $C_6$ ring system, particularly preferably an aromatic $C_6$ ring system, i.e. together with the cyclopentadienyl $C_5$ ring form, and/or two vicinal radicals $R^{1B}$-$R^{4B}$ are joined to form a heterocycle which contains at least one atom from the group consisting of N, P, O and S. Examples of such systems are an unsubstituted or substituted indenyl, benzindenyl, phenanthrenyl, fluorenyl or tetrahydroindenyl system, e.g. indenyl, 2-methylindenyl, 2-ethyl-indenyl, 2-isopropylindenyl, 3-methylindenyl, benzindenyl or 2-methylbenzindenyl. In particular, $R^{1B}$ and $R^{2B}$ together with the cyclopentadienyl system form a substituted or unsubstituted indenyl system.

The fused ring system may bear further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part, $NR^{11B}{}_2$, $N(SiR^{11B}{}_3)_2$, $OR^{11B}$, $OSiR^{11B}{}_3$ or $SiR^{11B}{}_3$, e.g. 4-methylindenyl, 4-ethylindenyl, 4-isopropylindenyl, 5-methylindenyl, 4-phenylindenyl, 5-methyl-4-phenylindenyl, 2-methyl-4-phenylindenyl or 4-naphthylindenyl.

As in the case of metallocenes, the monocyclopentadienyl complexes A) of the present invention may be chiral. Thus, one of the substituents $R^{1B}$-$R^{4B}$ of the cyclopentadienyl skeleton can have one or more chiral centers, or else the cyclopentadienyl system Cp can itself be enantiotopic, so that chirality is induced only when the cyclopentadienyl system is bound to the transition metal M (for formalisms regarding chirality in cyclopentadienyl compounds, cf. R. Halterman, Chem. Rev. 92, (1992), 965-994).

The bridge —$CR^{5B}R^{6B}$— between the cyclopentadienyl system Cp and the heteroaromatic A is an organic divalent bridge. —$CR^{5B}R^{6B}$— can be —$CH_2$—, —$CHCH_3$— or —$C(CH_3)^2$—. —$CR^{5B}R^{6B}$— is preferably —$CH_2$— or —$CHCH_3$—, particularly preferably —$CH_2$—. —$CR^{5B}R^{6B}$— is very particularly preferably bound both to the fused heterocycle or fused-on aromatic and to the cyclopentadienyl skeleton. Thus, if the heterocycle or aromatic is fused on in the 2,3 position of the cyclopentadienyl skeleton, —$CR^{5B}R^{6B}$— is preferably located in the 1 or 4 position of the cyclopentadienyl skeleton.

Examples of possible carboorganic substituents $R^{7B}$-$R^{10B}$ in A are the following: hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, and arylalkyl which may bear further alkyl groups as substituents, e.g. benzyl, o-, m-, p-methylbenzyl, 1- or 2-ethylphenyl, where two vicinal radicals $R^{7B}$ to $R^{10B}$ may also be joined to form a 5- or 6-membered ring or may also be substituted by halogens, e.g. fluorine, chlorine or bromine, or alkyl or aryl. $R^{7B}$-$R^{10B}$ are each preferably hydrogen, methyl, ethyl, n-propyl, isopropyl, n-butyl, isobutyl, tert-butyl, n-pentyl, n-hexyl, n-heptyl, n-octyl, benzyl or phenyl. In organosilicon substituents $SiR^{11B}{}_3$, possible radicals $R^{11B}$ are the same radicals mentioned in more detail above for $R^{11A}$, with two $R^{11B}$ also being able to be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl.

A is a substituted or fused heteroaromatic, six-membered ring system having 1, 2, 3, 4 or 5 nitrogen atoms in the heteroaromatic part which is bound to —$CR^{5B}R^{6B}$— or an unsubstituted, substituted or fused heteroaromatic, six-membered ring system having 2, 3, 4 or 5 nitrogen atoms in the heteroaromatic part which is bound to —$CR^{5B}R^{6B}$—, in particular 2-quinolyl or substituted 2-pyridyl. Examples of 6-membered heteroaryl groups, which can contain from two to five nitrogen atoms, are 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 6-membered heteroaryl groups may also bear $C_1$-$C_{10}$-alkyl groups, $C_6$-$C_{10}$-aryl groups, alkylaryl groups having from 1 to 10 carbon atoms in the alkyl part and 6-10 carbon atoms in the aryl part, trialkylsilyl groups or halogens such as fluorine, chlorine or bromine as substituents or be fused with one or more aromatics or heteroaromatics. Examples of benzo-fused 6-membered heteroaryl groups are 2-quinolyl, 3-cinnolyl, 2-quinazolyl, 4-quinazolyl, 2-quinoxalyl, 1-phenanthridyl and 1-phenazyl.

A can bind to the chromium either intermolecularly or intramolecularly. A is preferably bound intramolecularly to Cr. The synthesis to bind A to the cyclopentadienyl ring can be carried out, for example, by a method analogous to that of P. Jutzi and U. Siemeling in J. Orgmet Chem. (1995), 500, 175-185.

In particular, 1 $E^{1B}$-$E^{4B}$ is nitrogen and the others are carbon. A is particularly preferably 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethyl-2-pyrazinyl, 3,5,6-trimethyl-2-pyrazinyl, 2-quinolyl, 4-methyl-2-quinolyl, 6-methyl-2-quinolyl, 7-methyl-2-quinolyl, 2-quinoxalyl or 3-methyl-2-quinoxalyl.

Furthermore, preference is given to monocyclopentadienyl complexes in which all $E^{1B}$-$E^{4B}$ are carbon and at least one, preferably one, radical $R^{7B}$-$R^{10B}$ is $C_1$-$C_{20}$-alkyl, $C_2$-$C_{20}$-alkenyl, $C_6$-$C_{20}$-aryl, aryl, alkylaryl having from 1 to 10 carbon atoms in the alkyl part and 6-20 carbon atoms in the aryl part or $SiR^{11B}{}_3$. A is particularly preferably 6-methyl-2-pyridyl, 4-methyl-2-pyridyl, 5-methyl-2-pyridyl, 5-ethyl-2-pyridyl, 4,6-dimethyl-2-pyridyl or 6-benzyl-2-pyridyl.

Chromium is particularly preferably present in one of the oxidation states 2, 3 and 4, in particular 3. The chromium complexes can be obtained in a simple manner by reacting the appropriate metal salts, e.g. chromium chlorides, with the ligand anion (e.g. using a method analogous to the examples in DE 197 10615).

The monocyclopentadienyl complex A') can be present as a monomeric, dimeric or trimeric compound. It is possible, for example, for one or more ligands X to bridge two metal centers M. In the process of the present invention, preference is given to monocyclopentadienyl complexes A') of the formula (Cp-$CR^{5B}R^{6B}$-A)$CrX_k$ (VII), where the variable Cp-$CR^{5B}R^{6B}$-A is as defined above and its preferred embodiments are also preferred here and:

X are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, alkylaryl having 1-10 carbon atoms in the alkyl part and 6-20 carbon atoms in the aryl part, $NR^1R^2$, $OR^1$, $SR^1$, $SO_3R^1$, $OC(O)R^1$, CN, SCN, β-diketonate, CO, $BF_4^-$, $PF_6^-$ or a bulky noncoordinating anion, $R^1$-$R^2$ are each, Independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^3{}_9$, where the organic radicals $R^1$-$R^2$ may also be substituted by halogens or nitrogen- and oxygen-containing groups and two radicals $R^1$-$R^2$ may also be joined to form a five- or six-membered ring, $R^3$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two radicals $R^3$ may also be joined to form a five-or six-membered ring and k is 1, 2 or 3.

The embodiments and preferred embodiments mentioned above for Cp-$CR^{5B}R^{6B}$-A also apply individually and in combination to these preferred monocyclopentadienyl complexes A').

The ligands X can result, for example, from the choice of the corresponding starting chromium compounds which are used for the synthesis of the monocyclopentadienyl complexes A'), but can also be varied afterwards. Suitable ligands X are, in particular, the halogens fluorine, chlorine, bromine or iodine, in particular chlorine. Alkyl radicals such as methyl, ethyl, propyl, butyl, vinyl, allyl, phenyl or benzyl are also advantageous ligands X. Further possible ligands X are, purely by way of example and not in any way exhaustively, trifluoroacetate, $BF_4^-$, $PF_6^-$ and weakly coordinating or non-coordinating anions (cf., for example, Strauss in Chem. Rev. 1993, 93, 927-942) such as $B(C_6F_5)_4^-$.

Amides, alkoxides, sulfonates, carboxylates and β-diketonates are also particularly suitable ligands x. Variation of the radicals $R^1$ and $R^2$ enables, for example, physical properties such as solubility to be finely adjusted. Possible carboorganic substituents $R^1$-$R^2$ are, for example, the following: $C_1$-$C_{20}$-alkyl which may be linear or branched, for example methyl, ethyl, n-propyl, isopropyl, n-butyl, isobutyl, tert-butyl, n-pentyl, n-hexyl, n-heptyl, nil, n-nonyl, n-decyl or n-dodecyl, 5 to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and have an internal or terminal double bond, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N- or O-containing radicals, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl or arylalkyl which may be substituted by further alkyl groups, e.g. benzyl, o-, m-, p-methylbenzyl, 1- or 2-ethylphenyl, where $R^1$ may also be joined to $R^2$ to form a 5- or 6 membered ring and the organic radicals $R^1$-$R^2$ may also be substituted by halogens, e.g. fluorine, chlorine or bromine. In organosilicon substituents $SiR^3_3$, $R^3$ may be the same radicals as described In more detail above for $R^1$-$R^2$, with two $R^3$ also being able to be joined to form a 5- or 6-membered ring. Examples of substituents $SiR^3_3$ are trimethylsilyl, triethylsilyl, butyldimethylsilyl, tributylsilyl, triallylsilyl, triphenylsilyl and dimethylphenylsilyl. Preference is given to using $C_1$-$C_{10}$-alkyl such as methyl, ethyl, n-propyl, n-butyl, tert-butyl, n-pentyl, n-hexyl, n-heptyl, n-octyl and also vinyl, allyl, benzyl and phenyl as radicals $R^1$ and $R^2$. Some of these substituted ligands X are very particularly preferably used since they are obtainable from cheap and readily available starting materials. In a particularly preferred embodiment X is dimethylamide, methoxide, ethoxide, isopropoxide, phenoxide, naphthoxide, triflate, p-toluenesulfonate, acetate or acetylacetonate.

The number k of the ligands X depends on the oxidation state of the chromium. The number k can therefore not be specified in general terms. The oxidation state of the transition metals M in catalytically active complexes is usually known to a person skilled in the art Chromium is very probably present in the oxidation state +3. However, it is also possible to use complexes whose oxidation state does not correspond to that of the active catalyst. Such complexes can then be appropriately reduced or oxidized by means of suitable activators. Preference is given to using chromium complexes in the oxidation state +3.

Furthermore, we have found a process for preparing cyclopentadienyl system anions of the formula (VIIa),

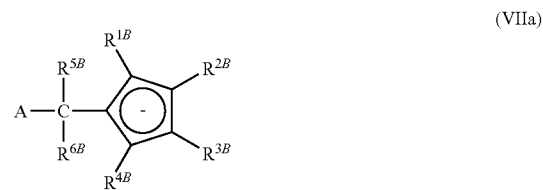

(VIIa)

where the variables have the following meanings:

$R^{1B}$-$R^{4B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms In the alkyl radical and 6-20 carbon atoms in the aryl radical, $NR^{5A}_2$, $N(SiR^{11B}_3)_2$, $OR^{11B}$, $OSiR^{11B}_3$, $SiR^{11B}_3$, $BR^{11B}_2$, where the organic radicals $R^{1B}$-$R^{4B}$ may also be substituted by halogens and two vicinal radicals $R^{1B}$-$R^{4B}$ may also be joined to form a five- or six-membered ring, $R^{5B}$, $R^{6B}$ are each hydrogen or methyl, A is

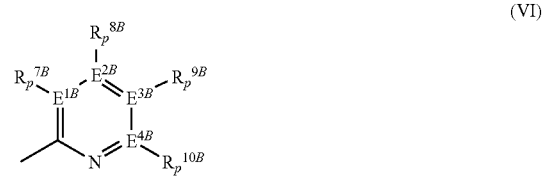

(VI)

where $E^{1B}$-$E^{4B}$ are each carbon or nitrogen, $R^{7B}$-$R^{10B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{11B}_3$, where the organic radicals $R^{7B}$-$R^{10B}$ may also bear halogens or nitrogen or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{11B}_3$ as substituents and two vicinal radicals $R^{7B}$-$R^{10B}$ may also be joined to form a five- or six-membered ring, $R^{11B}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{11B}$ may also be joined to form a five- or six-membered ring, p is 0 when $E^{1B}$-$E^{4B}$ is nitrogen and is 1 when $E^{1B}$-$E^{4B}$ is carbon, where at least one radical $R^{7B}$-$R^{10B}$ is $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{11B}_3$ and the organic radicals $R^{7B}$-$R^{10B}$ may also bear halogens or nitrogen or further $C_1$-$C_{20}$-alkyl groups, $C_2$-$C_{20}$- alkenyl groups, $C_6$-$C_{20}$-aryl groups, alkylaryl groups having from 1 to 10 carbon atoms in the alkyl part and 6-20 carbon atoms in the aryl part or $SiR^{5C}_3$ as substituents and two vicinal radicals $R^{7B}$-$R^{10B}$ may also be joined to form a five- or six-membered ring or at least one $E^{1B}$-$E^{4B}$ is nitrogen, which comprises the step a), where, in step a), a fulvene of the formula (VIIIa)

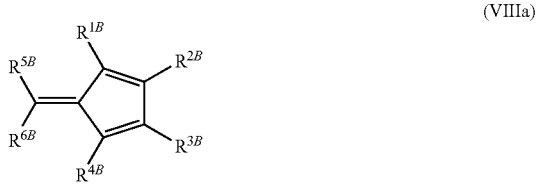

(VIIIa)

is reacted with an $A^-$ anion of the formula (VIIIa)

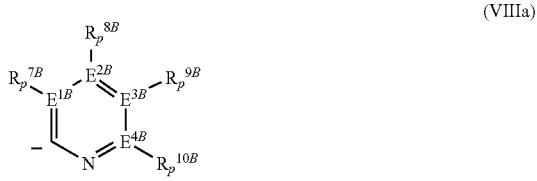

(VIIIa)

where the variables are each as defined above.

The variables and their preferred embodiments have been described above.

Fulvenes have been known for a long time and can be prepared, for example, as described by Freiesleben, Angew. Chem. 75 (1963), p. 576.

The counteraction of the cyclopentadienyl system anion (VIIa) is the cation of the $A^-$ anion. This is generally a metal of group 1 or 2 of the Periodic Table of the Elements which may bear further ligands. Particular preference is given to lithium, sodium or potassium cations which may also bear uncharged ligands such as amines or ethers and magnesium chloride or magnesium bromide cations which may likewise bear further uncharged ligands, in particular lithium, magnesium chloride or magnesium bromide cations.

The $A^-$ anion is usually obtained by a metal-halogen exchange reaction of A halide with a metal alkyl compound containing a metal of group 1 or 2, in particular lithium, magnesium chloride or magnesium bromide cations. Suitable metal alkyls are, for example, lithium alkyls, magnesium alkyls, magnesium (alkyl) halides or mixtures thereof. The molar ratio of metal alkyl compound to A halide is usually in the range from 0.4:1 to 100:1, preferably in the range from 0.9:1 to 10:1 and particularly preferably from 0.95:1 to 1.1:1. Examples of such reactions are described, inter alia, by Furukawa et al. in Tet. Lett. 28 (1987), 5845. As solvents, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The halogen-metal exchange can be carried out at from -100 to +160° C., in particular from -80 to 100° C. At temperatures above 40° C., preference is given to using aromatic or aliphatic solvents which contain no ethers or only small proportions of ethers.

Particularly preferred $A^-$ systems are 2-pyridinyl, 3-pyridazinyl, 2-pyrimidinyl, 4-pyrimidinyl, 2-pyrazinyl, 2-quinolyl, 3-cinnolyl, 2-quinazolyl or 4-quinazolyl.

The $A^-$ anion formed by metal-halogen exchange can be isolated but is preferably reacted with the fulvene (VIIIa) without further isolation. As solvents for the further reaction, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The deprotonation can be carried out at from -100 to +160° C., preferably from -80 to 100° C. and particularly preferably from 0 to 60° C. At temperatures above 40° C. preference is given to using aromatic or aliphatic solvents which contain no ethers or only small proportions of ethers.

The cyclopentadienyl system anion (VIIIa) obtained in this way can then be reacted further with the appropriate transition metal compound, e.g. chromium bichloride tris(tetrahydrofuran), to give the corresponding monocyclopentadienyl complex (A).

Furthermore, we have found a process for preparing cyclopentadiene systems of the formula (VIIb),

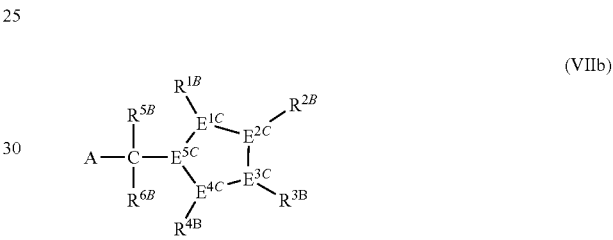

(VIIb)

where the variables have the following meanings:
$E^{1C}$-$E^{5C}$ are each carbon, where four adjacent $E^{1C}$-$E^{5C}$ form a conjugated diene system and the remaining $E^{1C}$-$E^{5C}$ additionally bears a hydrogen atom,
$R^{1B}$-$R^{4B}$ are each, independently of one another, hydrogen, $C_1$-$C_{20}$-alkyl, $C_2$-$C_{20}$-alkenyl, $C_6$-$C_{20}$-aryl, aryl, alkylaryl having from 1 to 10 carbon atoms in the alkyl part and 6-20 carbon atoms in the aryl part, $NR^{5A}_2$, $N(SiR^{11B}_3)_2$, $OR^{11B}$, $OSiR^{11B}_3$, $SiR^{11B}_3$, $BR^{11B}_2$, where the organic radicals $R^{1B}$-$R^{4B}$ may also be substituted by halogens and two vicinal radicals $R^{1B}$-$R^{4B}$ may also be joined to form a five- or six-membered ring,
$R^{5B}$,$R^{6B}$ are each hydrogen or methyl,
A is

(VI)

where
$E^{1B}$-$E^{4B}$ are each carbon or nitrogen,
$R^{7B}$-$R^{10B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms In the aryl part or $SiR^{11B}_3$, where the organic radicals $R^{7B}$-$R^{10B}$ may also bear halogens or nitrogen or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{11B}{}_3$ as substituents and two vicinal radicals $R^{7B}$-$R^{10B}$ may also be joined to form a five- or six-membered ring, $R^{11B}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{11B}$ may also be joined to form a five- or six-membered ring, p is 0 when $E^{1B}$-$E^{4B}$ is nitrogen and is 1 when $E^{1B}$-$E^{4B}$ is carbon, where at least one $R^{7B}$-$R^{10B}$ is $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{11B}{}_3$ and the organic radicals $R^{7B}$-$R^{10B}$ may also bear halogens or nitrogen or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{5C}{}_3$ as substituents and two vicinal radicals $R^{7B}$-$R^{10B}$ may also be joined to form a five- or six-membered ring or at least one $E^{1B}$-$E^{4B}$ is nitrogen, which comprises the following step:

a') reaction of an A-$CR^{5B}R^{6B-}$ anion with a cyclopentenone system of the formula (IX)

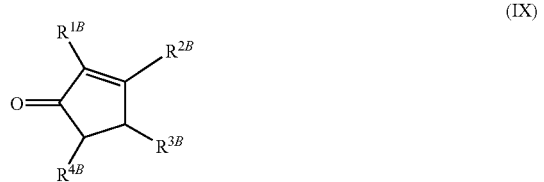

where the variables are as defined above.

The variables and their preferred embodiments have been described above and those definitions also apply in this process.

The cation of the A-$CR^{5B}R^{6B-}$ anion is generally a metal of group 1 or 2 of the Periodic Table of the Elements which may bear further ligands. Particular preference is given to lithium, sodium or potassium cations which may also bear uncharged ligands such as amines or ethers and magnesium chloride or magnesium bromide cations which may likewise bear further uncharged ligands.

The A-$CR^{5B}R^{6B-}$ anion is usually obtained by deprotonation of A-$CR^{5B}R^{6B}H$. This can be carried out using strong bases such as lithium alkyls, sodium hydride, sodium amides, sodium alkoxides, sodium alkyls, potassium hydride, potassium amides, potassium alkoxides, potassium alkyls, magnesium alkyls, magnesium (alkyl) halides or mixtures thereof. The molar ratio of base to A-$CR^{5B}R^{6B}H$ is usually in the range from 0.4:1 to 100:1, preferably in the range from 0.9:1 to 10:1 and particularly preferably from 0.95:1 to 1.1:1. Examples of such deprotonations are described in L. Brandsma, Preparative polar organometallic chemistry 2, pp. 133-142.

As solvents In the deprotonation step, it is possible to use all aprotic solvents, In particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The deprotonation can be carried out at from $-100$ to $+160°$ C., in particular from $-80$ to $100°$ C. At temperatures above $40°$ C., preference is given to using aromatic or aliphatic solvents which contain no ethers or only small proportions of ethers as solvent.

A-$CR^{5B}R^{6B}H$ is particularly preferably a group of the formula (VIIIb)

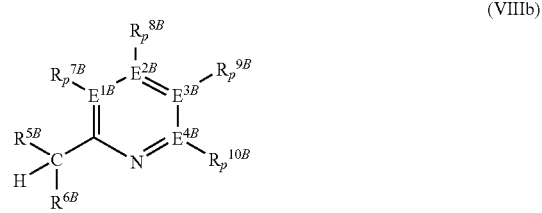

where the variables are as defined above.

The $CR^{6B}R^{6B}H$ group is preferably located in the ortho position relative to a nitrogen atom of A. A-$CR^{5B}R^{6B}H$ is preferably 2,6-lutidine, 2,4-lutidine, 2,5-lutidine, 2,3-cycloheptenopyridine, 5-ethyl-2-methylpyridine, 2,4,6-collidine, 3-methylpyridazine, 4-methylpyrimidine, 4,6-dimethylpyrimidine, 2-methylpyrazine, 2-ethylpyrazine, 2,6-dimethylpyrazine, 2,5-dimethylpyrazine, 2,3-dimethylpyrazine, 2,3-diethylpyrazine, tetrahydroquinoxaline, tetramethylpyrazine, quinaldine, 2,4-dimethylquinoline, 2,6-dimethylquinoline, 2,7-dimethylquinoline, 2-methylquinoxaline, 2,3-dimethylquinoxaline or neocuproin.

The A-$CR^{5B}R^{6B}$ anion formed after deprotonation can be isolated but is preferably reacted with the cyclopentenone (IX) without further isolation. As solvents for the further reaction, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reaction with the cyclopentenone (IX) can be carried out at from $-100$ to $+160°$ C., preferably from $-80$ to $100°$ C. and particularly preferably from 0 to $60°$ C. At temperatures above $40°$ C., preference is given to using aromatic or aliphatic solvents which contain no ethers or only small proportions of ethers as solvent.

The cyclopentenolate formed by reaction of the A-$CR^{5B}R^{6B-}$ anion with the cyclopentenone (IX) is usually protonated before dehydration. This can be carried out, for example, by means of small amounts of acid, for example HCl, or by means of an aqueous work-up. The intermediate obtained in this way, viz. a cyclopentenol, is subsequently dehydrated. This is often carried out with addition of catalytic amounts of acid, e.g. HCl or p-toluenesulfonic acid, or Iodine. Dehydration can be carried out at from $-10$ to $+160°$ C., preferably from 0 to $100°$ C. and particularly preferably from 20 to $80°$ C. As solvents, it is possible to use aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. Particularly useful solvents are toluene or heptane. Water separators are often also utilized for the dehydration.

This method of preparing the cyclopentadiene systems (VIIIb) is particularly advantageous since it is carried out using simple starting materials and gives good yields. The by-products formed (dehydration in the exo position) can be separated off in a simple manner by the further reactions to form the monocyclopentadienyl complex. The cyclopentadiene system (VIIb) obtained in this way can be deprotonated by customary methods, for example using potassium hydride or n-butyllithium, and reacted further with the appropriate transition metal compound, e.g. chromium trichloride tris (tetrahydrofuran), to give the corresponding monocyclopentadienyl complex (A'). The by-products undergo none of these reactions. Furthermore, the cyclopentadiene system (VIIb) can also be reacted directly with, for example, chromium amides to give the monocyclopentadienyl complex (A') in a manner analogous to the process in EP-A-742 046. The monocyclopentadienyl complexes of the present invention can be used alone or together with further components as catalyst systems for olefin polymerization.

For the monocyclopentadienyl complexes A) or A') to be able to be used in polymerization processes in the gas phase or in suspension, it is often advantageous to use the metallocenes in the form of a solid, i.e. for them to be applied to a solid support B). Furthermore, the supported monocyclopentadienyl complexes have a high productivity. The monocyclopentadienyl complexes A) or A') can therefore also, if desired, be immobilized on an organic or inorganic support B) and used in supported form in the polymerization. This enables, for example, deposits in the reactor to be avoided and the polymer morphology to be controlled. As support materials, preference is given to using silica gel, magnesium chloride, aluminum oxide, mesoporous materials, aluminosilicates, hydrotalcites and organic polymers such as polyethylene, polypropylene, polystyrene, polytetrafluoroethylene or polar functionalized polymers, e.g. copolymers of ethene and acrylic esters, acrolein or vinyl acetate.

Particular preference is given to a catalyst system comprising a monocyclopentadienyl complex A) or A') and at least one activating compound C) and also a support component B).

To obtain such a supported catalyst system, the unsupported catalyst system A) or A') can be reacted with a support component B). The order in which the support component B), the monocyclopentadienyl complex A) or A') and the activating compound C) are combined is in principle immaterial. The monocyclopentadienyl complex A) or A') and the activating compound C) can be immobilized independently of one another, e.g. in succession or simultaneously. Thus, the support component B) can firstly be brought into contact with the activating compound or compounds C) or the support component B) can firstly be brought into contact with the monocyclopentadienyl complex A) or A'). Preactivation of the monocyclopentadienyl complex A) or A') using one or more activating compounds C) before mixing with the support B) is also possible. In one possible embodiment, the metal complex (A) can also be prepared in the presence of the support material. A further method of immobilization is prepolymerization of the catalyst system with or without prior application to a support Immobilization is generally carried out in an inert solvent which can be removed by filtration or evaporation after immobilization has been carried out. After the individual process steps, the solid can be washed with suitable inert solvents such as aliphatic or aromatic hydrocarbons and dried. However, the use of the still moist, supported catalyst is also possible.

In a preferred method of preparing the supported catalyst system, at least one of the monocyclopentadienyl complexes A) or A') is brought into contact with at least one activating compound C) in a suitable solvent, preferably giving a soluble reaction product, an adduct or a mixture. The preparation obtained in this way is then mixed with the dehydrated or passivated support material, the solvent is removed and the resulting supported monocyclopentadienyl complex catalyst system is dried to ensure that all or most of the solvent has been removed from the pores of the support material. The supported catalyst is obtained as a free-flowing powder. Examples of the industrial implementation of the above process are described in WO 96/00243, WO 98140419 or WO 00/05277. A further preferred embodiment comprises firstly applying the activating compound C) to the support component B) and subsequently bringing this supported compound into contact with the monocyclopentadienyl complex A) or A').

As support component B), preference is given to using finely divided supports which can be any organic or inorganic solids. In particular, the support component B) can be a porous support such as talc, a sheet silicate such as montmorillonite, mica, an inorganic oxide or a finely divided polymer powder (e.g. a polyolefin or a polymer having polar functional groups).

The support materials used preferably have a specific surface area in the range from 10 to 1 000 $m^2/g$, a pore volume in the range from 0.1 to 5 ml/g and a mean particle size of from 1 to 500 µm. Preference is given to supports having a specific surface area in the range from 50 to 700 $m^2/g$, a pore volume in the range from 0.4 to 3.5 ml/g and a mean particle size in the range from 5 to 350 µm. Particular preference Is given to supports having a specific surface area In the range from 200 to 550 $m^2/g$, a pore volume in the range from 0.5 to 3.0 ml/g and a mean particle size of from 10 to 150 µm.

The inorganic support can be subjected to a thermal treatment, e.g. to remove adsorbed water. Such a drying treatment is generally carried out at from 80 to 300° C., preferably from 100 to 200° C. Drying at from 100 to 200° C. is preferably carried out under reduced pressure and/or under a blanket of inert gas (e.g. nitrogen), or the inorganic support can be calcined at from 200 to 1 000° C. to produce the desired structure of the solid and/or the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, the treatment of silica gel with $NH_4SiF_6$ or other fluorinating agents leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. ones based on polystyrene, polyethylene or polypropylene, via whose functional groups, for example ammonium or hydroxy groups, at least one of the catalyst components can be fixed.

Inorganic oxides suitable as support component B) may be found among the oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium or titanium and also corresponding oxide mixtures. Other inorganic oxides which can be used alone or in combination with the abovementioned preferred oxidic supports are, for example, MgO, CaO, AlPO$_4$, ZrO$_2$, TiO$_2$, B$_2$O$_3$ or mixtures thereof.

As solid support materials B) for catalysts for olefin polymerization, preference is given to using silica gels since particles whose size and structure make them suitable as supports for olefin polymerization can be produced from this material. Spray-dried silica gels comprising spherical agglomerates of smaller granular particles, i.e. primary particles, have been found to be particularly useful. The silica gels can be dried and/or calcined before use.

Further preferred supports B) are hydrotalcites and calcined hydrotalcites. In mineralogy, hydrotalcite is a natural mineral having the ideal formula

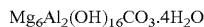

Mg$_6$Al$_2$(OH)$_{16}$CO$_3$.4H$_2$O whose structure is derived from that of brucite Mg(OH)$_2$. Brucite crystallizes in a sheet structure with the metal ions in octahedral holes between two layers of close-packed hydroxyl ions, with only every second layer of the octahedral holes being occupied. In hydrotalcite, some magnesium ions are replaced by aluminum ions, as a result of which the packet of layers gains a positive charge. This is compensated by the anions which are located together with water of crystallization in the layers in between.

Such sheet structures are found not only in magnesium-aluminum hydroxides, but also generally in mixed metal hydroxides of the formula

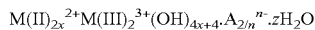

M(II)$_{2x}^{2+}$M(III)$_2^{3+}$(OH)$_{4x+4}$·A$_{2/n}^{n-}$·zH$_2$O which have a sheet structure and in which M(II) is a divalent metal such as Mg, Zn, Cu, Ni, Co, Mn, Ca and/or Fe and M(III) is a trivalent metal such as Al, Fe, Co, Mn, La, Ce and/or Cr, x is from 0.5 to 10 in steps of 0.5, A is an interstitial anion and n is the charge on the interstitial anion which can be from 1 to 8, usually from 1 to 4, and z is an integer from 1 to 6, in particular from 2 to 4. Possible interstitial anions are organic anions such as alkoxide anions, alkyl ether sulfates, aryl ether sulfates or glycol ether sulfates, inorganic anions such as, in particular, carbonate, hydrogencarbonate, nitrate, chloride, sulfate or B(OH)$_4^-$ or polyoxo metal anions such as Mo$_7$O$_{24}^{6-}$ or V$_{10}$O$_{28}^{6-}$. However, a mixture of a plurality of such anions can also be present.

Accordingly, all such mixed metal hydroxides having a sheet structure should be regarded as hydrotalcites for the purposes of the present invention.

Calcined hydrotalcites can be prepared from hydrotalcites by calcination, i.e. heating, by means of which the desired hydroxyl group content can be set. In addition, the crystal structure also changes. The preparation of the calcined hydrotalcites used according to the present invention is usually carried out at temperatures above 180° C. Preference is given to calcination for from 3 to 24 hours at from 250° C to 1 000° C., in particular from 400° C. to 700° C. It is possible for air or inert gas to be passed over the solid or a vacuum to be applied during this step.

On heating, the natural or synthetic hydrotalcites firstly give off water, i.e. drying occurs. On further heating, the actual calcination, the metal hydroxides are converted Into the metal oxides by elimination of hydroxyl groups and interstitial anions; OH groups or interstitial anions such as carbonate can also still be present in the calcined hydrotalcites. A measure of this is the weight loss on ignition. This is the weight loss experienced by a sample which is heated in two steps firstly for 30 minutes at 200° C. in a drying oven and then for 1 hour at 950° C. in a muffle furnace.

The calcined hydrotalcites used as component B) are thus mixed oxides of the divalent and trivalent metals M(II) and M(III), with the molar ratio of M(II) to M(III) generally being in the range from 0.5 to 10, preferably from 0.75 to 8 and in particular from 1 to 4. Furthermore, normal amounts of impurities, for example Si, Fe, Na, Ca or Ti and also chlorides and sulfates, can also be present.

Preferred calcined hydrotalcites B) are mixed oxides in which M(II) is magnesium and M(III) is aluminum. Such aluminum-magnesium mixed oxides are obtainable from Condea Chemie GmbH (now Sasol Chemie), Hamburg, under the trade name Puralox Mg.

Preference is also given to calcined hydrotalcites in which the structural transformation is complete or virtually complete. Calcination, i.e. transformation of the structure, can be confirmed, for example, by means of X-ray diffraction patterns.

The hydrotalcites, calcined hydrotalcites or silica gels employed are generally used as finely divided powders having a mean particle diameter d$_{50}$ of from 5 to 200 μm, preferably from 10 to 150 μm, particularly preferably from 15 to 100 μm and in particular from 20 to 70 μm, and usually have pore volumes of from 0.1 to 10 cm$^3$/g, preferably from 0.2 to 5 cm$^3$/g, and specific surface areas of from 30 to 1 000 m$^2$/g, preferably from 50 to 800 m$^2$/g and in particular from 100 to 600 m$^2$/g. The monocyclopentadienyl complexes of the present invention are preferably applied in such an amount that the concentration of monocyclopentadienyl complexes in the finished catalyst system is from 5 to 200 μmol, preferably from 20 to 100 μmol and particularly preferably from 25 to 70 μmol per g of support B).

Some of the monocyclopentadienyl complexes A) or A') have little polymerization activity on their own and are then brought into contact with an activator, viz. the component C), to be able to display good polymerization activity. For this reason, the catalyst system optionally further comprises, as component C), one or more activating compounds, preferably at least one activating compound C).

Suitable compounds C) which are able to react with the monocyclopentadienyl complex A) or A') to convert it into a catalytically active, or more active, compound are, for example, compounds such as an aluminoxane, a strong uncharged Lewis acid, an ionic compound having a Lewis-acid cation or an ionic compound containing a Brönsted acid as cation.

The amount of activating compounds to be used depends on the type of activator. In general, the molar ratio of metal complex A) or A') to activating compound C) can be from 1:0.1 to 1:10 000, preferably from 1:1 to 1:2 000.

As aluminoxanes, it is possible to use, for example, the compounds described in WO 00/31090. Particularly useful aluminoxanes are open-chain or cyclic aluminoxane compounds of the formula (X) or (XI)

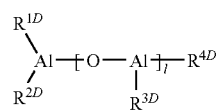

(X)

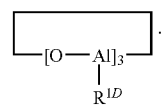

(XI)

where $R^{1D}$-$R^{4D}$ are each, independently of one another, a $C_1$-$C_6$-alkyl group, preferably a methyl, ethyl, butyl or isobutyl group, and 1 is an integer from 1 to 40, preferably from 4 to 25.

A particularly useful aluminoxane compound is methylaluminoxane.

These oligomeric aluminoxane compounds are usually prepared by controlled reaction of a solution of trialkylaluminum, in particular trimethylaluminum, with water. In general, the oligomeric aluminoxane compounds obtained in this way are in the form of mixtures of both linear and cyclic chain molecules of various lengths, so that 1 is to be regarded as a mean. The aluminoxane compounds can also be present in admixture with other metal alkyls, usually aluminum alkyls. Aluminoxane preparations suitable as component C) are commercially available.

Furthermore, modified aluminoxanes in which some of the hydrocarbon radicals have been replaced by hydrogen atoms or alkoxy, aryloxy, siloxy or amide radicals can also be used as component C) in place of the aluminoxane compounds of the formula (X) or (XI).

It has been found to be advantageous to use the monocyclopentadienyl complexes A) or A') and the aluminoxane compounds in such amounts that the atomic ratio of aluminum from the aluminoxane compounds including any aluminum alkyl still present to the transition metal from the monocyclopentadienyl complex A) or A') is in the range from 1:1 to 2 000:1, preferably from 10:1 to 500:1 and in particular in the range from 20:1 to 400:1.

A further class of suitable activating components C) are hydroxyaluminoxanes. These can be prepared, for example, by addition of from 0.5 to 1.2 equivalents of water, preferably from 0.8 to 1.2 equivalents of water, per equivalent of aluminum to an alkylaluminum compound, in particular triisobutylaluminum, at low temperatures, usually below 0° C. Such compounds and their use in olefin polymerization are described, for example, in WO 00/24787. The atomic ratio of aluminum from the hydroxyaluminoxane compound to the transition metal from the monocyclopentadienyl complex A) or A') is usually in the range from 1:1 to 100:1, preferably from 10:1 to 50:1 and In particular in the range from 20:1 to 40:1. Preference is given to using a monocyclopentadienyl metal dialkyl compound A) or A').

As strong, uncharged Lewis acids, preference is given to compounds of the formula (XII)

$$M^{2D}X^{1D}X^{2D}X^{3D} \quad (XII)$$

where $M^{2D}$ is an element of group 13 of the Periodic Table of the Elements, in particular B, Al or Ga, preferably B, $X^{1D}$, $X^{2D}$ and $X^{3D}$ are each hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryls, preferably pentafluorophenyl.

Further examples of strong, uncharged Lewis acids are given in WO 00/31090.

Compounds of this type which are particularly useful as component C) are boranes and boroxins such as trialkylborane, triarylborane or trimethylboroxin. Particular preference is given to using boranes which bear at least two perfluorinated aryl radicals. Particular preference is given to compounds of the formula (XII) in which $X^{1D}$, $X^{2D}$ and $X^{3D}$ are identical, preferably tris(pentafluorophenyl)borane.

Suitable compounds C) are preferably prepared by reaction of aluminum or boron compounds of the formula (XII) with water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4,4',5,5',6,6'-nonafluorobiphenyl. Examples of combinations of compounds of the formula (XII) with Brönsted acids are, in particular, trimethylaluminum/pentafluorophenol, trimethylaluminum/1-bis(pentafluorophenyl)methanol, trimethylaluminum/4-hydroxy-2,2',3,3',4,4',5, 5',6,6'-nonafluorobiphenyl, triethylaluminum/pentafluorophenol and triisobutylaluminum/pentafluorophenol and triethylaluminum/4,4'-dihydroxy-2, 2',3,3',5,5',6,6'-octafluorobiphenyl hydrate.

In further suitable aluminum and boron compounds of the formula (XII), $R^{1D}$ is an OH group. Examples of compounds of this type are boronic acids and borinic acids, in particular borinic acids having perfluorinated aryl radicals, for example $(C_6F_6)_2BOH$.

Strong uncharged Lewis acids suitable as activating compounds C) also include the reaction products of a boronic acid with two equivalents of an aluminum trialkyl or the reaction products of an aluminum trialkyl with two equivalents of an acidic fluorinated, in particular perfluorinated, hydrocarbon compound such as pentafluorophenol or bis(pentafluorophenyl)borinic acid.

The suitable ionic compounds having Lewis acid cations include salt-like compounds of the cation of the formula (XIII)

$$[((M^{3D})^{a+})Q_1Q_2 \ldots Q_z]^{d+} \quad (XIII)$$

where $M^{3D}$ is an element of groups 1 to 16 of the Periodic Table of the Elements, $Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups, a is an integer from 1 to 6 and z is an integer from 0 to 5, d corresponds to the difference a-z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane, or optionally a base, preferably an organic nitrogen-containing base, for example an amine, an aniline derivative or a nitrogen heterocycle. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acid, particular preference is given to protonated aniline or aniline derivatives. Preferred cations are N,N-dimethylanilinium, N,N-dimethylcyclohexylammonium and N,N-dimethylbenzylammonium and also derivatives of the latter two.

Compounds containing anionic boron heterocycles as are described in WO 97/36937 are also suitable as component C), in particular dimethylanilinium boratabenzene or trityl boratabenzene.

Preferred ionic compounds C) contain borates which bear at least two perfluorinated aryl radicals. Particular preference is given to N,N-dimethylanilinium tetrakis(pentafluorophenyl)borate and in particular N,N-dimethylcyclohexylammonium tetrakis(pentafluorophenyl)borate, N,N-dimethylbenzylammonium tetrakis(pentafluorophenyl)borate or trityl tetrakispentafluorophenylborate.

It is also possible for two or more borate anions to be joined to one another, as in the dianion $[(C_6F_5)_2B-C_6F_4-B(C_6F_5)_2]^{2-}$, or the borate anion can be bound via a bridge to a suitable functional group on the support surface.

Further suitable activating compounds C) are listed in WO 00/31090.

The amount of strong, uncharged Lewis acids, ionic compounds having Lewis-acid cations or ionic compounds containing Brönsted acids as cations is preferably from 0.1 to 20 equivalents, more preferably from 1 to 10 equivalents and particularly preferably from 1 to 2 equivalents, based on the monocyclopentadienyl complex A) or A').

Suitable activating compounds C) also include boron-aluminum compounds such as di[bis(pentafluorophenyl)boroxy]methylalane. Examples of such boron-aluminum compounds are those disclosed in WO 99/06414.

It is also possible to use mixtures of all the abovementioned activating compounds C). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane or a boroxin.

Both the monocyclopentadienyl complexes A) or A') and the activating compounds C) are preferably used in a solvent, preferably an aromatic hydrocarbon having from 6 to 20 carbon atoms, in particular xylenes, toluene, pentane, hexane, heptane or a mixture thereof.

A further possibility is to use an activating compound C) which can simultaneously be employed as support B). Such systems are obtained, for example, from an inorganic oxide by treatment with zirconium alkoxide and subsequent chlorination, for example by means of carbon tetrachloride. The preparation of such systems is described, for example, in WO 01/41920.

The catalyst system can further comprise, as additional component D), a metal compound of the formula (XX),

$$M^G(R^{1G})_{r^G}(R^{2G})_{s^G}(R^{3G})_{t^G} \quad (XX)$$

where $M^G$ is Li, Na, K, Be, Mg, Ca, Sr, Ba, boron, aluminum, gallium, indium, thallium, zinc, in particular Li, Na, K, Mg, boron, aluminum or Zn, $R^{1G}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part, $R^{2G}$ and $R^{3G}$ are each hydrogen, halogen, $C_1$-$C_{10}$-alkyl, $C_6$-$C_{15}$-aryl, alkylaryl, arylalkyl or alkoxy each having from 1 to 20 carbon atoms in the alkyl radical and from 6 to 20 carbon atoms in the aryl radical, or alkoxy containing $C_1$-$C_{10}$-alkyl or $C_6$-$C_{15}$-aryl, $r^G$ is an integer from 1 to 3 and $s^G$ and $t^G$ are integers from 0 to 2, with the sum $r^G+s^G+t^G$ corresponding to the valence of $M^G$, where the component D) is usually not identical to the component C). It is also possible to use mixtures of various metal compounds of the formula (XX).

Among the metal compounds of the formula (XX), preference is given to those in which $M^G$ is lithium, magnesium, boron or aluminum and $R^{1G}$ is $C_1$-$C_{20}$-alkyl.

Particularly preferred metal compounds of the formula (XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-n-octylmagnesium, tri-n-hexylaluminum, triisobutylaluminum, tri-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound D) is used, it is preferably present in the catalyst system in such an amount that the molar ratio of $M^G$ from formula (XX) to transition metal from monocyclopentadienyl compound A) or A') is from 2 000:1 to 0.1:1, preferably from 800:1 to 0.2:1 and particularly preferably from 100:1 to 1:1.

In general, the metal compound D) of the formula (XX) is used as constituent of a catalyst system for the polymerization or copolymerization of olefins. Here, the metal compound D) can be used, for example, for preparing a catalyst solid comprising the support B) and/or can be added during or shortly before the polymerization. The metal compounds D) used can be identical or different. It is also possible, particularly when the catalyst solid does not contain any activating component C), for the catalyst system to further comprise, in addition to the catalyst solid, one or more activating compounds C) which are identical to or different from any compounds D) present in the catalyst solid.

To prepare the catalyst systems of the present invention, preference is given to immobilizing at least one of the components A) or A') and/or C) on the support B) by physisorption or by means of chemical reaction, i.e. covalent binding of the components, with reactive groups of the support surface. The order in which the support component B), the component A) or A') and any component C) are combined is immaterial. The components A) or A') and C) can be added independently of one another or simultaneously or in premixed form to B). After the individual process steps, the solid can be washed with suitable inert solvents such as aliphatic or aromatic hydrocarbons.

In a preferred embodiment the monocyclopentadienyl complex A) or A') is brought into contact with the activating compound C) in a suitable solvent, usually giving a soluble reaction product, an adduct or a mixture. The preparation obtained in this way is then brought into contact with the support B), which may have been pretreated, and the solvent is completely or partly removed. This preferably gives a solid in the form of a free-flowing powder. Examples of the industrial implementation of the above process are described in WO 96/00243, WO 98/40419 or WO 00/05277. A further preferred embodiment comprises firstly applying the activating compound C) to the support B) and subsequently bringing this supported activating compound into contact with the monocyclopentadienyl complex A) or A').

The component D) can likewise be reacted in any order with the components A) or A') and, if desired, B) and C). For example, the monocyclopentadienyl complex A) can be brought into contact with the component(s) C) and/or D) either before or after being brought into contact with the olefins to be polymerized. Preactivation using one or more components C) prior to mixing with the olefin and further addition of the same or different components C) and/or D) after this mixture has bebg+en brought into contact with the olefin is also possible. Preactivation is generally carried out at 10-100° C., in particular 20-80° C.

Preference is given to D) firstly being brought into contact with component C) and then dealing with the components A) or A') and B) and any further C) as described above. In another preferred embodiment, a catalyst solid is prepared from the components A) or A'), B) and C) as described above and this is brought into contact with the component D) during, at the beginning of or shortly before the polymerization. Preference is given to D) firstly being brought into contact with the α-olefin to be polymerized and the catalyst solid comprising the components A) or A'), B) and C) as described above subsequently being added.

It is also possible for the catalyst system firstly to be prepolymerized with α-olefins, preferably linear $C_2$-$C_{10}$-1-alkenes and in particular ethylene or propylene, and the resulting prepolymerized catalyst solid then to be used in the actual polymerization. The mass ratio of catalyst solid used in the prepolymerization to monomer polymerized onto it is usually in the range from 1:0.1 to 1:1 000, preferably from 1:1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the catalyst system. The molar ratio of additives to transition metal compound A) or A') is usually from 1:1 000 to 1 000:1, preferably from 1:5 to 20:1.

In the process of the present invention for the copolymerization of ethylene with α-olefins, α-olefins are generally hydrocarbons having terminal double bonds, with the hydrocarbon also being able to bear functional groups containing atoms of groups 14 to 17 of the Periodic Table of the Elements. Suitable monomers Include functionalized olefinically unsaturated compounds such as acrolein, esters or amide derivatives of acrylic or methacrylic acid, for example acrylates, methacrylates or acrylonitrile, or vinyl esters, for example vinyl acetate. Preference is given to nonpolar olefinic compounds which contain only carbon atoms, including aryl-substituted α-olefins. Particularly preferred α-olefins are linear or branched $C_2$-$C_{12}$-1-alkenes, in particular linear $C_2$-$C_{10}$-1-alkenes such as ethene, propene, 1-butene, 1-pentene, 1-hexene, 1-heptene, 1-octene, 1-decene or branched $C_2$-$C_{10}$-1-alkenes such as 4-methyl-1-pentene, conjugated and nonconjugated dienes such as 1,3-butadiene, 1,5hexadiene or 1,7-octadiene or vinylaromatic compounds such as styrene or substituted styrene. It is also possible to polymerize mixtures of various α-olefins. Preference is given to polymerizing at least one α-olefin selected from the group consisting of ethene, propene, 1-butene, 1-pentene, 1-hexene, 1-heptene, 1-octene and 1-decene.

Mixtures of two or more α-olefins can also be copolymerized with ethene. Preference is given to using monomer mixtures containing at least 50 mol % of ethene.

The process of the present invention for the polymerization of ethylene with α-olefins can be combined with all industrially known polymerization processes at from −60 to 350° C. and pressures of from 0.5 to 4 000 bar. The polymerization can be carried out in a known manner in bulk, in suspension, in the gas phase or in a supercritical medium in the customary reactors used for the polymerization of olefins. It can be carried out batchwise or preferably continuously in one or more stages. High-pressure polymerization processes in tube reactors or autoclaves, solution processes, suspension processes, stirred gas-phase processes or gas-phase fluidized-bed processes are all possible.

The polymerizations are usually carried out at from −60 to 350° C. under pressures of from 0.5 to 4 000 bar at mean residence times of from 0.5 to 5 hours, preferably from 0.5 to 3 hours. The advantageous pressure and temperature ranges for carrying out the polymerizations usually depend on the polymerization method. In the case of high-pressure polymerization processes, which are usually carried out at pressures of from 1 000 to 4 000 bar, in particular from 2 000 to 3 500 bar, high polymerization temperatures are generally also set. Advantageous temperature ranges for these high-pressure polymerization processes are from 200 to 320° C., in particular from 220 to 290° C. In the case of low-pressure polymerization processes, a temperature which is at least a few degrees below the softening temperature of the polymer is generally set. These polymerization processes are preferably carried out at from 50 to 180° C., more preferably from 70 to 120° C. In the case of suspension polymerizations, the polymerization is usually carried out in a suspension medium, preferably an inert hydrocarbon such as isobutane or a mixture of hydrocarbons, or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out batchwise, e.g. in stirring autoclaves, or continuously, e.g. in tube reactors, preferably in loop reactors. Particular preference is given to employing the Phillips PF process as described in U.S. Pat. No. 3,242,150 and U.S. Pat. No. 3,248,179. The gas-phase polymerization is generally carried out at from 30 to 125° C. at pressures of from 1 to 50 bar.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed phase, in which part of the circulating gas is cooled to below the dew point and is recirculated as a two-phase mixture to the reactor. It is also possible to use a multizone reactor in which two polymerization zones are linked to one another and the polymer is passed alternately through these two zones a number of times. The two zones can also have different polymerization conditions. Such a reactor is described, for example, in WO 97/04015. The different or identical polymerization processes can also, if desired, be connected in series so as to form a polymerization cascade, for example in the Hostalen process. A parallel reactor arrangement using two or more identical or different processes is also possible. Furthermore, molar mass regulators, for example hydrogen, or customary additives such as antistatics can also be used in the polymerizations.

The ethylene copolymer of the present Invention can also be a constituent of a polymer mixture. Thus, for example, two or three different ethylene copolymers according to the present invention which may differ, for example, in their density and/or their molar mass distribution and/or their short chain branching distribution can be mixed with one another. They can also be produced by means of a cascade polymerization.

Further useful polymer mixtures comprise
(E) from 1 to 99% by weight of one or more of the ethylene copolymers according to the present invention and
(F) from 1 to 99% by weight of a polymer which is different from (E), where the percentages by weight are based on the total mass of the polymer mixture.

Polymer mixtures comprising
(E) from 1 to 99% by weight of one of the ethylene copolymers according to the present invention, in particular from 30 to 95% by weight and particularly preferably from 50 to 85% by weight, and
(F) from 1 to 99% by weight of a polyolefin which is different from (E), in particular from 5 to 70% by weight and particularly preferably from 15 to 50% by weight, where the percentages by weight are based on the total mass of the polymer mixture, are particularly suitable.

The type of further polymer components (F) in the mixture depends on the intended use of the mixture. The mixture can be obtained, for example, by blending with one or more additional LLDPEs or HDPEs or LDPEs or PPs or polyamides or polyesters. Alternatively, the polymer mixture can be produced by simultaneous polymerization using a monocyclopentadienyl complex and one or more catalyst systems which are likewise active in the polymerization of olefins. Suitable catalysts for producing the polymer blends or for simultaneous polymerization are, in particular, classical Ziegler-Natta catalysts based on titanium, classical Phillips catalysts based on chromium oxides, metallocenes, in particular complexes of metals of groups 3 to 6 of the Periodic Table of the Elements containing one, two or three cyclopentadienyl, indenyl and/or fluorenyl systems, viz. constrained geometry complexes (cf., for example, EP-A 0 416 815 or EP-A 0 420 436), nickel and palladium bisimine systems (for their preparation, see WO 9803559 A1) or iron and cobalt pyridinebisimine compounds (for their preparation, see WO 9827124 A1). However, in the case of a mixture consisting of various polymers according to the present invention, it is also possible to use another chromium complex A). The further polymerization catalysts can likewise be supported on one and the same support or different supports.

The ethylene copolymer of the present invention can also form mixtures having a broad or bimodal molar mass distribution with other olefin polymers, in particular ethylene homopolymers and copolymers. These mixtures can be obtained either by means of the above-described simultaneous presence of a further catalyst suitable for the polymerization of olefins or by subsequent blending of the separately prepared polymers or copolymers.

The blends comprising olefin copolymers according to the present invention can also further comprise two or three other olefin polymers or copolymers. These can be, for example, LDPEs (blends thereof are described, for example, in DE-A1-19745047) or polyethylene homopolymers (blends thereof are described, for example, in EP-B-100843), LLDPEs (as described, for example, in EP-B-728160 or WO-A-90/03414), LLDPE/LDPE (WO 95/27005 or EP-B1-662989). The proportion of copolymers according to the present invention is at least 40-99% by weight, preferably 50-90% by weight, based on the total mass of the polymer mixture.

The ethylene copolymers, polymer mixtures and blends can further comprise known auxiliaries and/or additives such as processing stabilizers, stabilizers against the action of light and heat, customary additives such as lubricants, antioxidants, antiblocking agents and antistatics, and also, if desired, colorants. The type and amount of these additives are known to those skilled in the art.

Furthermore, it has been found that mixing in small amounts of fluoroelastomers or thermoplastic polyesters can give further improvements in the processing properties of the polymers of the present invention. Such fluoroelastomers are known as such as processing aids and are commercially available, e.g. under the trade names Viton® and Dynamar® (cf., for example, U.S. Pat. No. 3,125,547). They are preferably added in amounts of from 10 to 1 000 ppm, particularly preferably from 20 to 200 ppm, based on the total mass of the polymer mixture according to the present invention.

The polymers of the present invention can also be modified subsequently by grafting, crosslinking, hydrogenation, functionalization or other modification reactions known to those skilled in the art.

The production of the polymer blends by mixing can be carried out by all known methods. It can be achieved, for example, by feeding the powder components into a granulation apparatus, e.g. a twin-screw kneader (ZSK), Farrel kneader or Kobe kneader. It is also possible to process a granulated mixture directly on a film production plant.

The polymers and polymer mixtures of the present invention are very useful, for example, for the production of films on blown film and cast film plants at high outputs. The films made of the polymer mixtures display very good mechanical properties, high shock resistance and high tear strength combined with very good optical properties, in particular transparency and gloss. They are particularly useful for the packaging sector, for example as heat sealing films, and both for labels and sacks and for the food sector. Furthermore, the films display only a slight blocking tendency and can therefore be passed through machines without additions of lubricants and antiblocking agents or with additions of only small amounts thereof.

Owing to their good mechanical properties, the ethylene copolymers of the present invention are likewise suitable for the production of fibers and moldings, in particular pipes and crosslinkable pipes. They are likewise suitable for blow molding, rotomolding or Injection molding. They are also useful as compounding components, bonding agents and as rubber component in polypropylene, in particular in polypropylene compounds having high Impact toughnesses.

The following examples illustrate the invention.

EXAMPLES

NMR samples were dispensed under inert gas and, if appropriate, melted in. The solvent signals served as internal standard in the $^1$H- and $^{13}$C-NMR spectra, and the chemical shifts were then converted into chemical shifts relative to Tetramethylsilane.

The density [g/cm$^3$] was determined in accordance with ISO 1183.

The determination of the molar mass distributions and the means $M_n$, $M_w$, and $M_w/M_n$ derived therefrom was carried out by means of high-temperature gel permeation chromatography using a method based on DIN 55672 under the following conditions: solvent 1,2,4-trichlorobenzene, flow: 1 ml/min, temperature: 140° C., calibration using PE standards.

The TREF analyses were carried out under the following conditions: solvent: 1,2,4-trichlorobenzene, flow: 1 ml/min, healing rate: 1° C./min, amount of polymer: 5-10 mg, support: diatomaceous earth (kieselgur).

The CDBI was determined as described in WO-A-93/03093.

Figure 2:
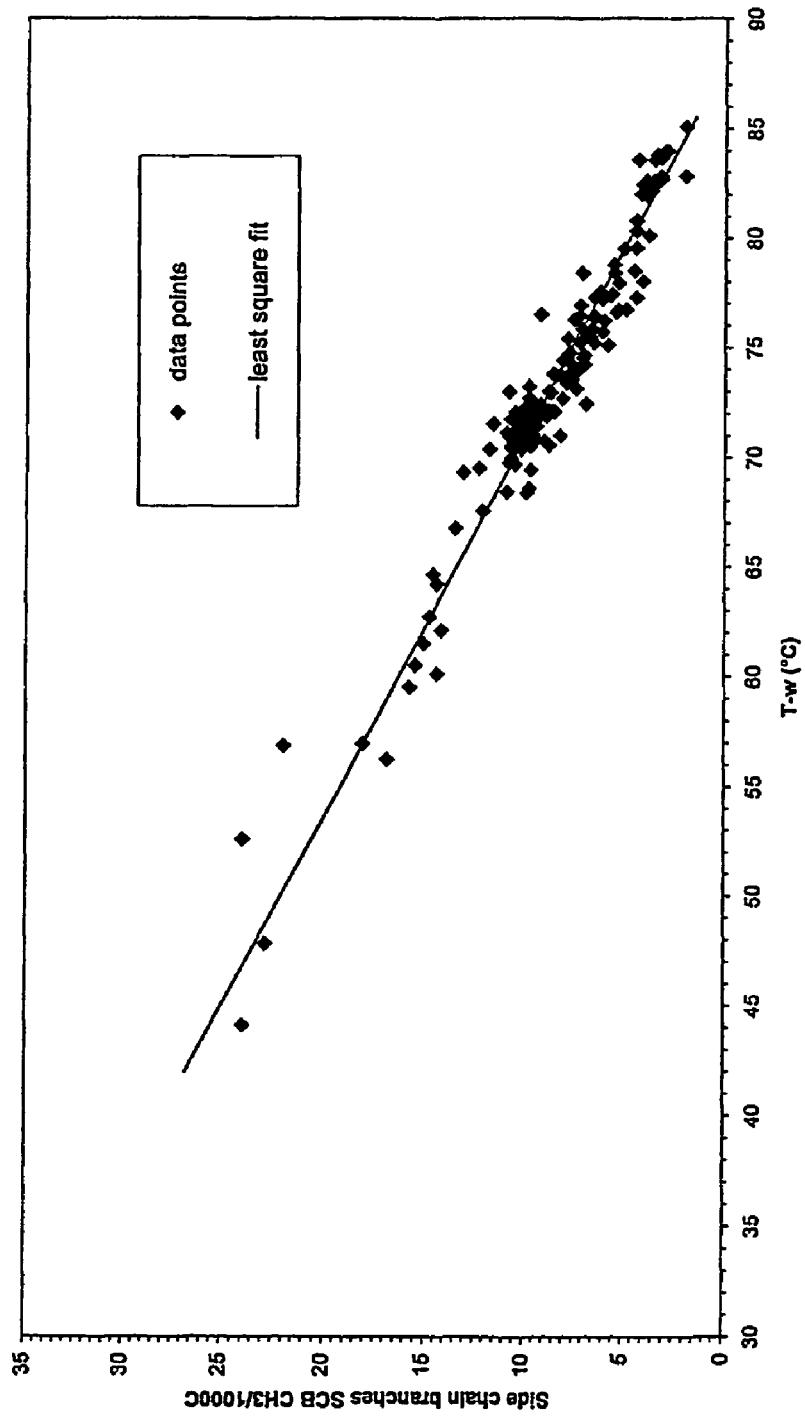

The Crystaf® measurements were carried out on an instrument from Polymer Char, P.O. Box 176, E-46980 Paterna, Spain, using 1,2-dichlorobenzene as solvent and the data were processed using the associated software. The Crystaf® temperature-time curve is depicted in FIG. 1. The differential Crystaf® curve shows the modality of the short chain branching distribution. To convert the Crystaf® curves obtained into $CH_3$ groups per 1 000 carbon atoms, the curve shown in FIG. 2 was used, depending on the type of comonomer employed. In this curve, the weight average temperature T-w is defined as the sum over all proportions by weight m-i multiplied by the temperature T-i, divided by the sum over all proportions by weight m-i:

$$T\text{-}w = \Sigma(m\text{-}i \cdot T\text{-}i)/\Sigma m\text{-}i$$

The degree of short chain branching ($CH_3/1\ 000\ C$) can thus be calculated simply in accordance with the following equation: $(CH_3/1\ 000\ C) = a \cdot T\text{-}w + b$ (see FIG. 2), in which the abbreviations are as follows:

| | | |
|---|---|---|
| weight average temperature | T-w: | (° C.) |
| slope | a: | −0.582 ($CH_3/1\ 000\ C$)/(° C.) |
| intercept | b: | 60.46 ($CH_3/1\ 000\ C$) |

The vinyl and vinyliden group content was determined by $^1$H-NMR.

The long chain branching rate λ was determined by light scattering as described in ACS Series 521, 1993, Chromatography of Polymers, Ed. Theodore Provder; Simon Pang and Alfred Rudin: Size-Exclusion Chromatographic Assessment of Long-Chain Branch Frequency in Polyethylenes, page 254-269.

Abbreviations used in the following table:

| | |
|---|---|
| Cat. | catalyst |
| t(poly) | duration of the polymerization |
| polymer | amount of polymer formed |
| $M_w$ | weight average molar mass |
| $M_n$ | number average molar mass |
| density | polymer density |
| Prod. | productivity of the catalyst in g of polymer obtained per mmol of catalyst (chromium complex) used per hour |

Example 1

1.1. Preparation of [2-(1H-inden-3-yl)methyl]-3,5,6-trimethylpyrazine

A mixture of 13.6 ml (0.1 mol) of 2,3,5,6-tetramethylpyrazine in 50 ml of tetrahydrofuran was cooled to −20° C. and 62.5 ml of n-butyllithium (1.6M in hexane, 0.1 mol) were subsequently added while stirring. The mixture was allowed to warm to room temperature while stirring. After stirring for a further 1 hour, the solution was cooled to −60° C. and a solution of 15 g (0.11 mol) of 1-indanone in 20 ml of tetrahydrofuran was added over a period of 15 minutes while stirring. The mixture was allowed to warm to room temperature while stirring and was stirred for a further 12 hours. The mixture was then hydrolyzed with 250 ml of dilute hydrochloric acid and allowed to stand. After 24 hours, the 2-[(2,3-dihydro-1H-inden-1-ylidenemethyl]-3,5,6-trimethylpyrazine hydrochloride (the by-product) which had precipitated was filtered off. The organic phase was separated off from the liquid phases and the aqueous phase was extracted twice with ethyl acetate. The aqueous phase was then neutralized with aqueous ammonia solution and extracted three times with 60 ml each time of methylene chloride. The organic phases were combined, dried over magnesium sulfate, the magnesium sulfate was filtered off and the solvent was distilled off. This gave 17.3 g of a mixture of 2-(1H-inden-3-ylmethyl)pyridine and 2-[(E)-2,3-dihydro-1H-inden-1-ylidenemethyl]-3,5,6-bimethylpyrazine (55% yield) and unreacted tetramethylpyrazine in a ratio of 10:3 (NMR). The mixture was used directly in the next step. NMR $^1$H (CDCl$_3$): 7.54 (d, 1H); 7.48 (d, 1H); 7.35 (t, 1H); 7.25 (t, 9H); 5.92 (br.s., 1H); 4.07 (br.s., 2H); 3.54 (br.s., 2H); 2.56 (s., 3H); 2.54 (s., 3H); 2.52 (s., 3H).

1.2. Preparation of (1-(2-(3,5,6-trimethylpyrazine)methyl)indenyl)chromium dichloride

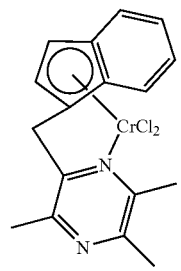

A solution of 7.25 g of the above mixture in 80 ml of tetrahydrofuran was cooled to −100° C. While stirring, 16 ml of a 15% strength n-butyllithium solution in hexane (0.0256 mol) were slowly added dropwise. After the addition was complete, the reaction mixture was stirred for a further one hour at −100° C. The mixture was subsequently allowed to warm to room temperature. After stirring for a further 2 hours, the solution was cooled to −60° C. and 10.2 g (0.0272 mol) of chromium trichloride tris(tetrahydrofuran) were added while stirring. The mixture was allowed to warm slowly to room temperature and was subsequently stirred for a further 10 hours at room temperature. The solid which had precipitated was filtered off, washed twice with diethyl ether and dried under reduced pressure. This gave 5.2 g of a green powder of which 4.2 g were recrystallized from a mixture of $CH_2Cl_2$-$Et_2O$. 3.1 g of (1-(2-3,5,6-bimethylpyrazine)methyl)indenyl)chromium dichloride (43%) were obtained.

Example 2

2.1. Preparation of [2-1H-inden-3-yl)-1-methylethyl]pyridine

A solution of 7.25 g (0.046 mol) of 2-bromopyridine in 20 ml of diethyl ether was cooled to −60° C. and a mixture of 28.7 ml of n-butyllithium (1.6M in hexane, 0.046 mol) and 70 ml of diethyl ether was subsequently added while stirring. The mixture was stirred for a further 15 minutes and a solution of 7.16 g (0.046 mol) of 1-(1-methylethylidene)-1-indene dissolved in 10 ml of ether was then added. The mixture was allowed to warm to room temperature and was hydrolyzed with 100 ml of dilute hydrochloric acid. The organic phase was separated off and the aqueous phase was extracted once with diethyl ether, after which the aqueous phase was neutralized with aqueous ammonia solution and extracted three times with 50 ml each time of chloroform. The organic phases were combined, dried over magnesium sulfate, the magnesium sulfate was filtered off and the solvent was distilled off. 0.54 g (5%) of [2-(1H-inden-3-yl)-1-methylethyl]-pyridine was obtained.

2.2. Preparation of (3-(2-pyridyl-1-methylethyl)indenyl)chromium dichloride

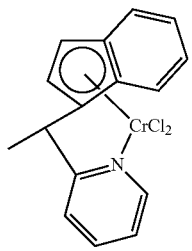

Comparative example 1

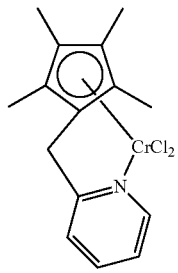

5-[(2-Pyridyl)methyl]-1,2,3,4-tetramethylcyclopentadienylchromium dichloride was prepared as described in WO 01/92346.

Polymerization

The polymerizations were carried out at 40° C. under argon in a 1 l four-necked flask provided with contact thermometer, stirrer with Teflon blade, heating mantle and gas inlet tube. The appropriate amount of MAO (10% strength solution in toluene, Cr:Al=1:500) was added to a solution of the amount indicated in table 1 of the respective complex in 250 ml of toluene and the mixture was heated to 40° C. on a water bath.

Shortly before introduction of ethylene, 3 ml of hexene were placed in the flask and about 20-40 l/h of ethylene were subsequently passed through the initial charge at atmospheric pressure. The remaining amount of hexene (7 ml) was introduced via a dropping funnel over a period of 15 minutes. After the time indicated in table 1 under a constant ethylene flow, the polymerization was stopped by addition of methanol HCl solution (15 ml of concentrated hydrochloric acid in 50 ml of methanol). 250 ml of methanol were subsequently added and the white polymer formed was filtered off, washed with methanol and dried at 70° C.

TABLE 1

| | | | | Polymerization results | | | | |
|---|---|---|---|---|---|---|---|---|
| Catalyst from Ex. | Amount of cat. [mg] | t(poly) [min] | Polymer [g] | Prod. [g/mmolCr h] | $M_w$ [g/mol] | $M_w/M_n$ | Density [g/cm$^3$] | Short chain branching CDBI distribution |
| 1 | 7.4 | 25 | 3.8 | 459 | 106 743 | 2.94 | 0.934 | <50% bimodal |
| 2 | 9.8 | 20 | 11.5 | 1 260 | 252 011 | 6.24 | n.d. | <50% bimodal |
| C1 | 7.7 | 20 | 12.8 | 1 692 | 28 067 | 4.61 | 0.94 | >50% monomodal |

Example 3

A solution of 0.54 g (0.0023 mol) of [2-1H-inden-3-yl)-1-methylethyl]pyridine in 20 ml of tetrahydrofuran was cooled to −100° C. 1.72 ml of a 15% strength n-butyllithium solution in hexane (0.0027 mol) were slowly added dropwise. After the addition was complete, the reaction mixture was stirred at −100° C. for a further 30 minutes. The mixture was subsequently allowed to warm to room temperature. After stirring for a further 1 hour, the solution was cooled to −60° C. and 1.1 g (0.0029 mol) of chromium trichloride bis(tetrahydrofuran) were added while stirring. The mixture was allowed to warm slowly to room temperature and was subsequently stirred for a further 10 hours at room temperature. The reaction mixture was then refluxed for 20 minutes and subsequently cooled to room temperature. The solid which had precipitated was filtered off, washed with diethyl ether and dried under reduced pressure. This gave 0.3 g of (3-(2-pyridyl-1-methylethyl)indenyl)chromium dichloride (37%).

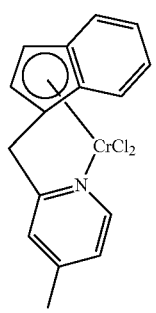

(3-(2-(4-Methylpyridyl)methyl)indenyl)chromium dichloride was prepared by a method analogous to example 1 but using the corresponding amount of 2,4-dimethylpyridine in place of tetramethylpyrazine.

The polymerization was carried out as described above at 40° C. under argon using hexene as comonomer and a polymerization time of 60 minutes. The activity of the complex (Cr: MAO=1:500) was 1 730 g/mmol of Cr h. The $M_w$ of the copolymer was 283 910 g/mol, the $M_w/M_n$ was 2.57. The copolymer had a CDBI of less than 50% and a bimodal short chain branching distribution (differential Crystaf® curve). The maxima of the Crystaf® peaks In the differential Crystaf® curve were at 12° C. and 33° C. The vinyl group content was 0.19 vinyl groups/1000 carbon atoms. The vinyliden group content was 0.52 vinyliden groups/1000 carbon atoms. The long chain branching rate λ less than 0.1 lcb/1000 carbon atoms.

We claim:

1. A copolymer of ethylene with α-olefins which comprises a molar mass distribution $M_w/M_n$ of from 1 to 8, a density of from 0.85 to 0.94 g/cm$^3$, a number average molar mass $M_n$ of from 10,000 g/mol to 4,000,000 g/mol, a CDBI of less than 50%, a vinyl group content of from 0.1 to 1 vinyl groups/1000 carbon atoms, a Lcb rate of from 0.001 to 0.09 Lcb/1000 carbon atoms, the copolymer comprising at least a bimodal short chain branching distribution, and wherein a side chain branching of the maxima of the individual peaks of the short chain branching distribution, as determined by crystallization analysis fractionation (CRYSTAF), of the copolymer of ethylene and the α-olefins is greater than 5 CH$_3$/1000 carbon atoms.

2. The copolymer of ethylene with α-olefins as claimed in claim 1, wherein the number average molar mass $M_n$ is from 150,000 g/mol to 1,000,000 g/mol.

3. The copolymer of ethylene with α-olefins as claimed in claim 1 which has at least one peak, as determined by CRYSTAF, of a differential distribution in the range from 15 to 40° C., and at least one further peak, as determined by CRYSTAF, of the differential distribution in the range from 25 to 80° C.

4. The copolymer of ethylene with α-olefins as claimed in claim 1, wherein the copolymer of ethylene with α-olefins comprise a trimodal short chain branching distribution.

5. A polymer mixture comprising:
(E) from 1 to 99% by weight of at least one ethylene copolymer comprising a molar mass distribution $M_w/M_n$ of from 1 to 8, a density of from 0.85 to 0.94 g/cm$^3$, a number average molar mass $M_n$ of from 10,000 g/mol to 4,000,000 g/mol, a CDBI of less than 50%, a vinyl group content of from 0.1 to 1 vinyl groups/1000 carbon atoms, a Lcb rate of from 0.001 to 0.09 Lcb/1000 carbon atoms, the copolymer comprising at least a bimodal short chain branching distribution, and wherein a side chain branching of the maxima of the individual peaks of the short chain branching distribution, as determined by crystallization analysis fractionation (CRYSTAF), of the ethylene copolymer is greater than 5 CH$_3$/1000 carbon atoms;
and
(F) from 1 to 99% by weight of a polymer which is different from (E),
where the percentages by weight are based on the total mass of the polymer mixture.

6. A fiber, film or molding comprising an ethylene copolymer comprising a molar mass distribution $M_w/M_n$ of from 1 to 8, a density of from 0.85 to 0.94 g/cm$^3$, a number average molar mass $M_n$ of from 10,000 g/mol to 4,000,000 g/mol, a CDBI of less than 50%, a vinyl group content of from 0.1 to 1 vinyl groups/1000 carbon atoms, a Lcb rate of from 0.001 to 0.09 Lcb/1000 carbon atoms, the copolymer comprising at least a bimodal short chain branching distribution, and wherein a side chain branching of the maxima of the individual peaks of the short chain branching distribution, as determined by crystallization analysis fractionation (CRYSTAF), of the ethylene copolymer is greater than 5 CH$_3$/1000 carbon atoms.

* * * * *